(12) United States Patent
Nozaki et al.

(10) Patent No.: US 9,303,101 B2
(45) Date of Patent: Apr. 5, 2016

(54) CATALYST FOR SYNTHESIZING POLYOLEFINS

(71) Applicants: THE UNIVERSITY OF TOKYO, Bunkyo-ku, Tokyo (JP); SHOWA DENKO K.K., Minato-ku, Tokyo (JP)

(72) Inventors: Kyoko Nozaki, Tokyo (JP); Brad Carrow, Tokyo (JP); Yoshikuni Okumura, Oita (JP); Junichi Kuroda, Oita (JP)

(73) Assignees: THE UNIVERSITY OF TOKYO, Tokyo (JP); SHOWA DENKO K.K., Tokyo (JP)

( * ) Notice: Subject to any disclaimer, the term of this patent is extended or adjusted under 35 U.S.C. 154(b) by 0 days.

(21) Appl. No.: 14/400,188

(22) PCT Filed: Apr. 30, 2013

(86) PCT No.: PCT/JP2013/062538
§ 371 (c)(1),
(2) Date: Nov. 10, 2014

(87) PCT Pub. No.: WO2013/168626
PCT Pub. Date: Nov. 14, 2013

(65) Prior Publication Data
US 2015/0099857 A1 Apr. 9, 2015

(30) Foreign Application Priority Data

May 11, 2012 (JP) ................................. 2012-109876
Mar. 4, 2013 (JP) ................................. 2013-041528

(51) Int. Cl.
*C08F 4/80* (2006.01)
*C07F 9/53* (2006.01)
*C07F 15/00* (2006.01)
*C08F 110/02* (2006.01)
*C08F 4/619* (2006.01)

(52) U.S. Cl.
CPC ................. *C08F 4/80* (2013.01); *C07F 9/5312* (2013.01); *C07F 9/5325* (2013.01); *C07F 15/006* (2013.01); *C08F 4/619* (2013.01); *C08F 110/02* (2013.01)

(58) Field of Classification Search
CPC .................................. C08F 4/80; C07F 15/006
USPC .................................. 526/172; 556/137, 136
See application file for complete search history.

(56) References Cited

U.S. PATENT DOCUMENTS

| 4,491,675 A | * | 1/1985 | Abatjoglou | .......... B01J 31/2495 |
| | | | | 502/161 |
| 4,689,437 A | | 8/1987 | Murray | |
| 5,482,596 A | * | 1/1996 | Wu | ......................... C07C 51/14 |
| | | | | 560/105 |
| 6,265,506 B1 | | 7/2001 | Goodall et al. | |

FOREIGN PATENT DOCUMENTS

| JP | 61502758 A | 11/1986 |
| JP | 2000143574 A | 5/2000 |
| JP | 2002501937 A | 1/2002 |
| JP | 2010265386 A | 11/2010 |
| JP | 2012504596 A | 2/2012 |
| WO | 8600889 A1 | 2/1986 |
| WO | 9938831 A1 | 8/1999 |
| WO | 2010038209 A1 | 4/2010 |

OTHER PUBLICATIONS

Brassat et al. J. Mol. Catal. A: Chemical 2000, 157, 41-58.*
Carrow, B.P.; Nozaki, K. J. Am. Chem. Soc. 2012, 134, 8802-8805.*
Brassat et al. Inorg. Chim. Acta 1998, 280, 150-162.*
Wasserscheid, P.; Hilgers, C.; Keim, W. J. Mol. Catal. A: Chemical 2004, 214, 83-90.*
Faller, J.W.; Friss, T.; Parr, J. J. Organomet. Chem. 2010, 695, 2644-2650.*
Marshall, W.J.; Grushin, V.V. Organometallics 2003, 22, 555-562.*
Farrer et al. Polyhedron 2010, 29, 254-261.*
Gladiali et al. Tetrahedron: Asymmetry 2004, 15, 1477-1485.*

(Continued)

*Primary Examiner* — Rip A Lee
(74) *Attorney, Agent, or Firm* — Sughrue Mion, PLLC

(57) ABSTRACT

The present invention relates to a method for producing a high-molecular-weight copolymer of polar group-containing allyl monomers comprising monomer units represented by formulae (3) and (4) (in the formulae, $R^1$ represents a hydrogen atom (H) or hydrocarbon group having 1 to 6 carbon atoms; $R^2$ represents —OH, —OCOR$^3$ ($R^3$ represents hydrocarbon group having 1 to 5 carbon atoms), —N(R$^4$)$_2$ ($R^4$ represents a hydrogen atom or hydrocarbon group having 1 to 5 carbon atoms); and n and m are a value representing the molar ratio of each of the monomer units), which has few branches and unsaturated group at the molecular end, by copolymerizing olefin and an allyl compound using a metal complex of group 10 elements in the periodic system represented by formula (I) as a catalyst.

The present invention enables providing a high-molecular-weight copolymer of polar group-containing allyl monomers, which copolymer has a novel structure, is available for various applications and has been considered to be difficult to synthesize by other polymerization methods such as radical polymerization; and a method for producing the same.

21 Claims, 6 Drawing Sheets

(56) References Cited

OTHER PUBLICATIONS

Bennett et al., "Formation of (Diphenylphosphino)naphthalenes by Double Insertion of (Alkynyl)diphenylphosphines into Nickel(0)—Benzyne Complexes", Organometallics, 2000, vol. 19, No. 8, pp. 1522 to 1533, Compounds 15a, 15b, 18.

Hibi et al., "Design of AB divinyl "template monomers" toward alternating sequence control in metal-catalyzed living radical polymerization", Polymer Chemistry, 2011, vol. 2, No. 2, pp. 341 to 347.

Hamada et al., "Synthesis and Application of New Chiral Bidentate Phosphine, 2,7-Di-terl-butyl-9,9-dimethyl-4,5-bis(methylphenylphosphino)xanthene", Tetrahedron Letters, 1997, vol. 38, No. 52, pp. 8961 to 8964.

Dong et al., "Design and synthesis of structurally well-defined functional polyolefins via transition metal-mediated olefin polymerization chemistry", Coordination Chemistry Reviews, 2006, vol. 250, pp. 47 to 65.

Padwa et al., "Functionally Substituted Poly($a$-Olefins)", Prog. Polym. Sci., 1989, vol. 14, pp. 811 to 833.

Johnson et al., "Copolymerization of Ethylene and Propylene with Functionalized Vinyl Monomers by Palladium(II) Catalysts", J. Am. Chem. Soc., 1996, vol. 118, No. 1, pp. 267 to 268.

Drent et al., "Palladium catalysed copolymerisation of ethene with alkylacrylates: polar comonomer built into the linear polymer chain", Chem. Comm., 2002, p. 744 to 745.

Ito et al., "Copolymerization of Vinyl Acetate with Ethylene by Palladium/Alkylphosphine-Sulfonate Catalysts", J. Am. Chem. Soc., 2009, vol. 131, No. 41, pp. 14606 to 14607.

Kochl et al., "Formation of Linear Copolymers of Ethylene and Acrylonitrile Catalyzed by Phosphine Sulfonate Palladium Complexes", J. Am. Chem. Soc., 2007, vol. 129, pp. 8948 to 8949.

International Search Report for PCT/JP2013/062538 dated Jul. 16, 2013.

Written Opinion of the ISA for PCT/JP2013/062538 dated Jul. 16, 2013.

Ingo Brassat et al; "Synthesis and catalytic activity of allyl, methallyl and methyl complexes of nickel(II) and palladium(II) with biphosphine monoxide ligands: oligomerization of ethylene and copolymerization of ethylene and carbon monoxide"; Journal of Molecular Catalysis A: Chemical 157 (2000); pp. 41-58.

Boris Neuwald, et al.; "Limits of Activity: Weakly Coordinating Ligands in Arylphosphinesulfonato Palladium(II) Polymerization Catalysts"; Organometallics; 2012; 31; pp. 3128-3137.

Peter Wasserscheid et al; "Ionic liquids: polar, but weakly coordinating solvents for the first biphasic oligomerisation of ethene to higher [alpha]-olefins with cationic Ni complexes"; Chemical Communications—Chemcom; No. 13, Jan. 1, 2001; pp. 1186-1187; XP55241746.

P. Wasserscheid et al; "Polymer Synthesis in Ionic Liquids"; Ionic Liquids in Synthesis; Wiley-VCH; Jan. 1, 2002; pp. 319-335; XP008073473.

Partial Supplementary European Search Report issued Jan. 25, 2016 for corresponding European Patent Application No. 13787262.8.

* cited by examiner

CATALYST FOR SYNTHESIZING POLYOLEFINS

CROSS REFERENCE TO RELATED APPLICATIONS

This application is a National Stage of International Application No. PCT/JP2013/062538, filed on Apr. 30, 2013, which claims priority from Japanese Patent Application No. 2012-109876, filed on May 11, 2012, and Japanese Patent Application No. 2013-041528, filed on Mar. 4, 2013, the contents of all of which are incorporated herein by reference in their entirety.

TECHNICAL FIELD

The present invention relates to a novel organometallic compound; a method for producing the same; a catalyst for synthesizing polyolefins (a catalyst compound for polymerization of vinyl monomers and for copolymerization of non-polar olefins and polar olefins); and a method for producing a (co)polymer using the catalyst.

BACKGROUND ART

Although polyolefins typified by polyethylene and polypropylene have been used versatilely, they are not suitable for all uses. Polyolefins are inherently non-polar, and therefore inferior in the properties such as adhesiveness, and persistence, print performance and affinity of dyes, and limited in their usefulness. However, it is known that such properties can be remarkably improved in functionalized polyolefins obtained by incorporating a small amount of polar functional groups in polyolefins.

In an effort to expand the application range of polyolefins, methods for incorporating polar functional groups into polyolefins have been reported (Non-patent documents 1, 2 and the like). Among these methods, the most direct method is to copolymerize olefin monomers with industrially useful polar vinyl monomers as shown in the following formula.

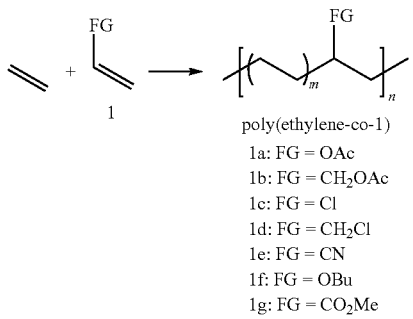

poly(ethylene-co-1)
1a: FG = OAc
1b: FG = CH$_2$OAc
1c: FG = Cl
1d: FG = CH$_2$Cl
1e: FG = CN
1f: FG = OBu
1g: FG = CO$_2$Me Coordination-insertion polymerization (coordination-addition polymerization) of olefins and polar vinyl monomers using a transition metal catalyst was proposed as a useful method for synthesizing functionalized polyolefins having a predetermined polymer structure, molecular weight distribution and amount of comonomer to be incorporated. As a late transition metal complex as a catalyst for coordination-insertion polymerization of olefins and polar vinyl monomers, the most successful one to date is the catalyst in which α-diimine or phosphine sulfonate ion is coordinated (Patent Document 1, Non-patent Documents 3 and 4). Generally, a highly-linear microstructure of polymer can be obtained by a palladium and nickel catalyst in which a phosphine-sulfonate ion is coordinated. Meanwhile, a palladium and nickel catalyst in which α-diimine is coordinated serves as a catalyst for forming a highly-branched polymer. Among these two important catalysts, it has been reported that the catalyst in which a phosphine-sulfonate ion is coordinated exhibits much higher activity in the copolymerization with polar vinyl monomers such as vinyl acetate, acrylonitrile, vinyl chloride and vinyl ether, compared to the catalyst in which α-diimine is coordinated (Non-patent Documents 5, 6 and the like).

However, a transition metal complex in which phosphine-sulfonate ion is coordinated has not yet been put to practical use.

Also, a method for copolymerizing ethylene and methyl acrylate using a nickel complex having an iminoamide ligand has been proposed (Patent Document 2), but the method has not yet been put to practical use, either.

PRIOR ART

Patent Document

Patent Document 1: U.S. Pat. No. 4,689,437
Patent Document 2: JP-A-2010-265386

Non-Patent Document

Non-patent Document 1: Chem. Rev., 2006, 250, 47
Non-patent Document 2: Prog. Polym. Sci., 1989, 14, 811
Non-patent Document 3: J. Am. Chem. Soc., 1996, 118, 267
Non-patent Document 4: Chem. Commun., 2002, 744
Non-patent Document 5: J. Am. Chem. Soc., 2009, 131, 14606-14607
Non-patent Document 6: J. Am. Chem. Soc., 2007, 129, 8948

SUMMARY OF THE INVENTION

Problems to be Solved by the Invention

An object of the present invention is to provide a catalyst composition for polymerizing polyolefins, which composition contains a novel organometallic compound and has higher activity than a conventional transition metal complex in which a phosphine-sulfonate ion is coordinated.

Method to Solve the Problem

A critical structural feature of a catalyst containing phosphine-sulfonate ester is that there exist one strong σ-donor ligand and one weak σ-donor ligand. To date, a catalyst having high activity in copolymerization of olefins and various polar monomers has been limited to a phosphine-sulfonate ester type. The present inventors thought that a complex containing a bidentate ligand having an asymmetry structure of a strong σ-donor ligand and one weak σ-donor ligand other than the combination of phosphine and sulfonate ester anion can promote formation of a highly-linear random copolymer in the coordination-insertion polymerization, and have studied various bidentate ligands. As a result, the present inventors have found that a novel cationic palladium complex to which bisphosphine monoxide (BPMO) is coordinated is applicable to a catalyst for polymerization of ethylene and a number of polar vinyl monomers and accomplished the present invention.

That is, the present invention relates to an organometallic compound described in [1] to [21] below, a catalyst composition for (co)polymerization described in [22] to [23] below, a method for producing copolymers described in [24] to [26] below, and a method for producing an organometallic compound described in [27] to [28] below.

[1] An organometallic compound containing bisphosphine monoxide (BPMO) represented by formula (I) and a metal center M comprising elements belonging to Group 10 in the periodic system forming a complex with BPMO

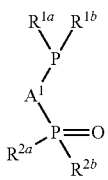

(in the formula, $R^{1a}$, $R^{1b}$, $R^{2a}$ and $R^{2b}$ may be the same or different with each other, and independently represent a substituted or unsubstituted alkyl group having 1 to 14 carbon atoms, a substituted or unsubstituted cycloalkyl group having 3 to 14 carbon atoms, a substituted or unsubstituted biphenyl group or a substituted or unsubstituted aryl group; a pair of $R^{1a}$ and $R^{1b}$ and a pair of $R^{2a}$ and $R^{2b}$ may be bonded to form a ring structure; and $A^1$ represents an arylene group, a monocyclic heteroarylene group, bivalent heterocyclic group, alkylene group having 1 to 2 carbon atoms, cycloalkylene group having 3 to 10 carbon atoms, alkenylene group having 2 to 8 carbon group, or cycloalkenylene group having 3 to 10 carbon atoms).

[2] The organometallic compound as described in [1] above, represented by formula (II)

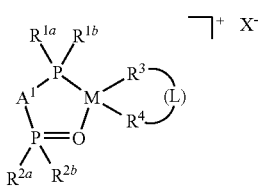

(in the formula, M, $R^{1a}$, $R^{1b}$, $R^{2a}$, $R^{2b}$ and $A^1$ have the same meanings as in [1] above; and $R^3$ represents a hydrogen atom, alkyl group having 1 to 10 carbon atoms, alkenyl group having 2 to 10 carbon atoms or bivalent group represented by $A^2$ ($A^2$ represents arylene group, monocyclic heteroarylene group, monocyclic cycloalkylene group, monocyclic cycloalkenylene group, monocyclic heterocycloalkylene group, monocyclic heterocycloalkenylene group, heterocyclic group or C2-C4 alkylene group); $R^4$ represents a neutral electron-donating ligand; $R^3$ and $R^4$ may be crosslinked; when $R^3$ and $R^4$ are crosslinked, L represents a single bond or a bivalent group selected from alkylene group, haloalkylene group, alkenylene group and alkynilene group; and when $R^3$ and $R^4$ are not crosslinked (that is, when L does not exist), $R^4$ needs not to exist; and $X^-$ represents a counterion of the cationic organometallic compound).

[3] The organometallic compound as described in [2] above, wherein ligand $R^4$ is:

(i) selected from pyridine, substituted pyridine, a nitrile compound, ammonia, alkylamine, substituted alkylamine, arylamine and substituted arylamine; or (ii) represented by formula (1)

(in the formula, W represents C or S; Z is selected from O, S, NH or $NR^a$ ($R^a$ represents alkyl group or aryl group) and Y needs not to exist; when Y exists, Y is selected from O, S, NH or $NR^b$ ($R^b$ represents alkyl group or aryl group); $R^5$ represents a substituted or unsubstituted alkyl group having 1 to 10 carbon atoms, $-OR^c$ ($R^c$ represents alkyl group or aryl group) or $-NR^d{}_2$ ($R^d$ represents alkyl group or aryl group)).

[4] The organometallic compound as described in any one of [1] to [3] above represented by formula (III)

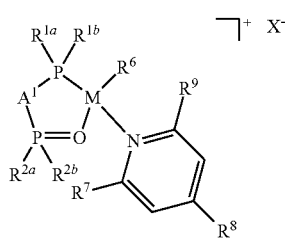

(in the formula, M, $R^{1a}$, $R^{1b}$, $R^{2a}$, $R^{2b}$, $A^1$ and $X^-$ have the same meanings as in formula (I) in [1] above and formula (II) in [2] above; $R^6$ represents alkyl group having 1 to 10 carbon atoms, alkenyl group or aryl group; $R^7$, $R^8$ and $R^9$ independently represent alkyl group or alkoxy group having 1 to 4 carbon atoms).

[5] The organometallic compound as described in any one of [1] to [3], represented by formula (IIa)

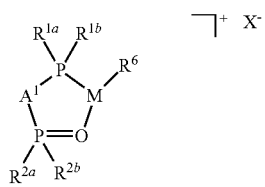

(in the formula, M, $R^{1a}$, $R^{1b}$, $R^{2a}$, $R^{2b}$, $R^6$, $A^1$ and $X^-$ have the same meanings as in [1] to [3] above).

[6] The organometallic compound as described in [4] or [5] above, wherein A1 is substituted or unsubstituted phenylene group, substituted or unsubstituted naphthylene group or substituted or unsubstituted methylene group.

[7] The organometallic compound as described in any one of [4] to [6] above, wherein $R^{1a}$, $R^{1b}$, $R^{2a}$ and $R^{2b}$ independently represent branched alkyl group having 3 to 6 carbon atoms.

[8] The organometallic compound as described in any one of [1] to [7] above, wherein both of $R^{1a}$ and $R^{1b}$ are isopropyl group or t-butyl group.

[9] The organometallic compound as described in any one of [1] to [8] above, wherein both of $R^{2a}$ and $R^{2b}$ are t-butyl group.

[10] The organometallic compound as described in any one of [4] to [9] above, wherein $X^-$ is selected from $SbF_6-$, $BPh_4-$, $BArF_4-$ ($ArF_4-=[3,5-(CF_3)_2C_6H_3]_4-$), $BF_4-$ and $PF_6-$.

[11] The organometallic compound as described in any one of [4] to [10] above, wherein M is palladium.
[12] The organometallic compound as described in any one of [1] to [3] above, represented by formula (IV)

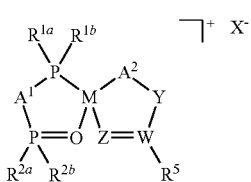

(IV)

(in the formula, M, $R^{1a}$, $R^{1b}$, $R^{2a}$, $R^{2b}$, $R^5$, $A^1$, $A^2$, Y, Z, W and $X^-$ have the same meanings as in [1] to [3] above).
[13] The organometallic compound as described in [12] above, wherein $A^1$ is a substituted or unsubstituted phenylene group, a substituted or unsubstituted naphthylene group or a substituted or unsubstituted methylene group.
[14] The organometallic compound as described in [12] or [13] above, represented by formula (V)

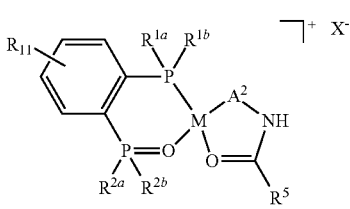

(V)

(in the formula, M, $R^{1a}$, $R^{1b}$, $R^{2a}$, $R^{2b}$, $A^2$, $R^5$ and $X^-$ have the same meanings as in [1] to [3] above; $R^{11}$ may not exist or represents alkyl group having 1 to 10 carbon atoms, 1 to 4 of which exist on a benzene ring, and the existing two or more $R^{11}$'s may be the same or different with each other).
[15] The organometallic compound as described in [14] above, wherein $A^2$ is substituted or unsubstituted phenylene group or naphthylene group.
[16] The organometallic compound as described in [15] above, represented by formula (VI)

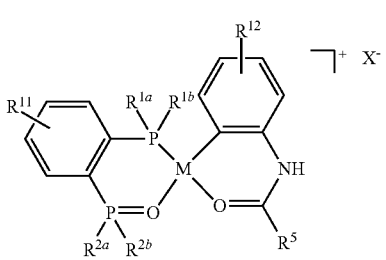

(VI)

(in the formula, M, $R^{1a}$, $R^{1b}$, $R^{2a}$, $R^{2b}$, $R^5$, $R^{11}$ and $X^-$ have the same meanings as in [1] to [3] and [14] above).
[17] The organometallic compound as described in any one of [12] to [16] above, wherein $R^{1a}$, $R^{1b}$, $R^{2a}$ and $R^{2b}$ are independently branched alkyl group having 3 to 14 carbon atoms.
[18] The organometallic compound as described in any one of [12] to [17] above, wherein both of $R^{1a}$ and $R^{1b}$ are isopropyl group.

[19] The organometallic compound as described in any one of [12] to [18] above, wherein both of $R^{2a}$ and $R^{2b}$ are t-butyl group.
[20] The organometallic compound as described in any one of [12] to [19] above, wherein $X^-$ is selected from $SbF_6^-$, $BPh_4^-$, $BArF_4^-$, $BF_4^-$ and $PF_6^-$.
[21] The organometallic compound as described in any one of [12] to [20] above, wherein M is palladium.
[22] A catalyst composition for polymerizing vinyl monomers, which contains the organometallic compound described in any one of [1] to [21] above.
[23] A catalyst composition for copolymerizing non-polar olefins and polar olefins, which contains the organometallic compound described in any one of [1] to [21] above.
[24] A method for producing copolymers, comprising a process of reacting non-polar olefins with polar olefins under polymerization conditions in the presence of the catalyst composition containing the organometallic compound described in any one of [1] to [21] above.
[25] The method for producing copolymers as described in [24] above, wherein polar olefins are represented by formula (VII)

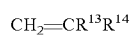

$$CH_2=CR^{13}R^{14} \quad (VII)$$

(in the formula, $R^{13}$ represents a hydrogen atom or methyl group; $R^{14}$ represents —$COOR^{15}$, —CN, —$OCOR^{15}$, —$OR^{15}$, —$CH_2$—$OCOR^{15}$, —$CH_2OH$, —$CH_2$—$N(R^{16})_2$ or —$CH_2$-Hal ($R^{15}$ represents a hydrogen atom, alkyl group having 1 to 5 carbon atoms or aryl group having 6 to 18 carbon atoms; $R^{16}$ represents a hydrogen atom, alkyl group having 1 to 5 carbon atoms, aryl group having 6 to 18 carbon atoms or alkoxycarbonyl group; and Hal represents a halogen atom)).
[26] The method for producing copolymers as described in [25] above, wherein $R^{14}$ is —$CH_2$—$OCOR^{15}$, —$CH_2OH$, —$CH_2$—$N(R^{16})_2$ or —$CH_2$-Hal ($R^{15}$, $R^{16}$ and Hal have the same meanings as described in [25] above).
[27] A method for producing an organometallic compound represented by formula (III)

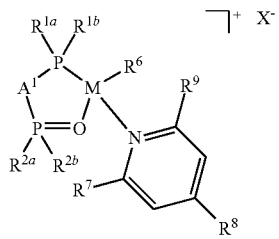

(III)

(in the formula, M, $R^{1a}$, $R^{1b}$, $R^{2a}$, $R^{2b}$, $R^6$, $R^7$, $R^8$, $R^9$, $A^1$ and X have the meanings as set forth below), comprising:
(1) A process of reacting free bisphosphine monoxide (BPMO) represented by formula (I)

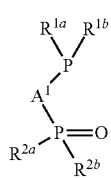

(I)

(in the formula, $R^{1a}$, $R^{1b}$, $R^{2a}$ and $R^{2b}$ may be the same or different with each other, and independently represent a substituted or unsubstituted alkyl group having 1 to 14 carbon atoms, a substituted or unsubstituted cycloalkyl group having 3 to 14 carbon atoms, a substituted or unsubstituted biphenyl group or a substituted or unsubstituted aryl group; a pair of $R^{1a}$ and $R^{1b}$ and a pair of $R^{2a}$ and $R^{2b}$ may be bonded to form a ring structure; and $A^1$ represents an arylene group, a monocyclic heteroarylene group, heterocyclic group, alkylene group having 1 to 2 carbon atoms, cycloalkylene group having 3 to 10 carbon atoms, alkenylene group having 2 to 8 carbon group, or cycloalkenylene group having 3 to 10 carbon atoms) and (1,5-cyclooctadiene) $MR^6Xa$ (M represents an element belonging to Group 10 in the periodic system; $R^6$ represents alkyl group having 1 to 10 carbon atoms, alkenyl group or aryl group; and Xa represents a halogen atom); and (2) A process of treating the generated (BPMO)(1,5-cyclooctadiene) $MR^6Xa$ complex with a metal salt represented by $M^2X$ ($M^2$ represents a monovalent metal ion selected from Ag, Li, Na and K; and X represents a counteranion selected from $SbF_6$, $BPh_4$, $BArF_4$, $BF_4$ and $PF_6$) and a compound represented by formula (2)

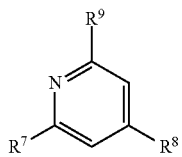

(2)

(in the formula, $R^7$, $R^8$ and $R^9$ independently represent a hydrogen atom, alkyl group having 1 to 4 carbon atoms or alkoxy group).

[28] A method for producing an organometallic compound represented by formula (IVa)

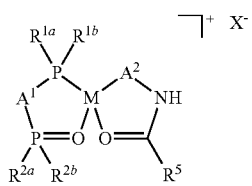

(IVa)

(in the formula, M, $R^{1a}$, $R^{1b}$, $R^{2a}$, $R^{2b}$, $R^5$, $A^1$, $A^2$ and X have the meanings as set forth below), comprising:

(1) A process of reacting free bisphosphine monoxide (BPMO) represented by formula (I)

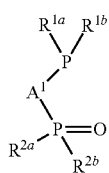

(I)

(in the formula, $R^{1a}$, $R^{1b}$, $R^{2a}$, $R^{2b}$ and $A^1$ have the meanings as described in [1] above) with a compound represented by formula (3)

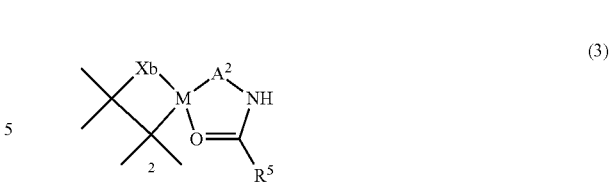

(3)

(in the formula, M represents an element belonging to Group 10 in the periodic system; $A^2$ represents an arylene group, a monocyclic heteroarylene group, a monocyclic cycloalkylene group, a monocyclic cycloalkenylene group, a monocyclic heterocycloalkylene group, a monocyclic heterocycloalkenylene group, heterocyclic or C2-C4 alkylene group; $R^5$ represents substituted or unsubstituted alkyl group having 1 to 10 carbon atoms, $OR^c$ ($R^c$ represents alkyl group or aryl group) or $NR^d_2$ ($R^d$ represents alkyl group or aryl group); and Xb represents halogen); and (2) a process of adding a metal salt represented by $M^2X$ ($M^2$ represents a monovalent metal ion selected from Ag, Li, Na and K; and X represents a counteranion selected from $SbF_6$, $BPh_4$, $BArF_4$, $BF_4$ and $PF_6$) to the reaction product of process (1).

Effects of the Invention

The catalyst composition containing a novel organometallic compound of the present invention has a high activity in the coordination-insertion polymerization of ethylene and polar vinyl monomers. By using the catalyst composition of the present invention, a highly-linear polymer can be obtained and further, a copolymer in which polar monomers are randomly distributed in polymer chains can be obtained. Thus, the catalyst composition containing a novel organometallic compound of the present invention is extremely useful since it enables the production of industrially-useful functionalized polyolefin.

MODE FOR CARRYING OUT THE INVENTION

Figure 1:
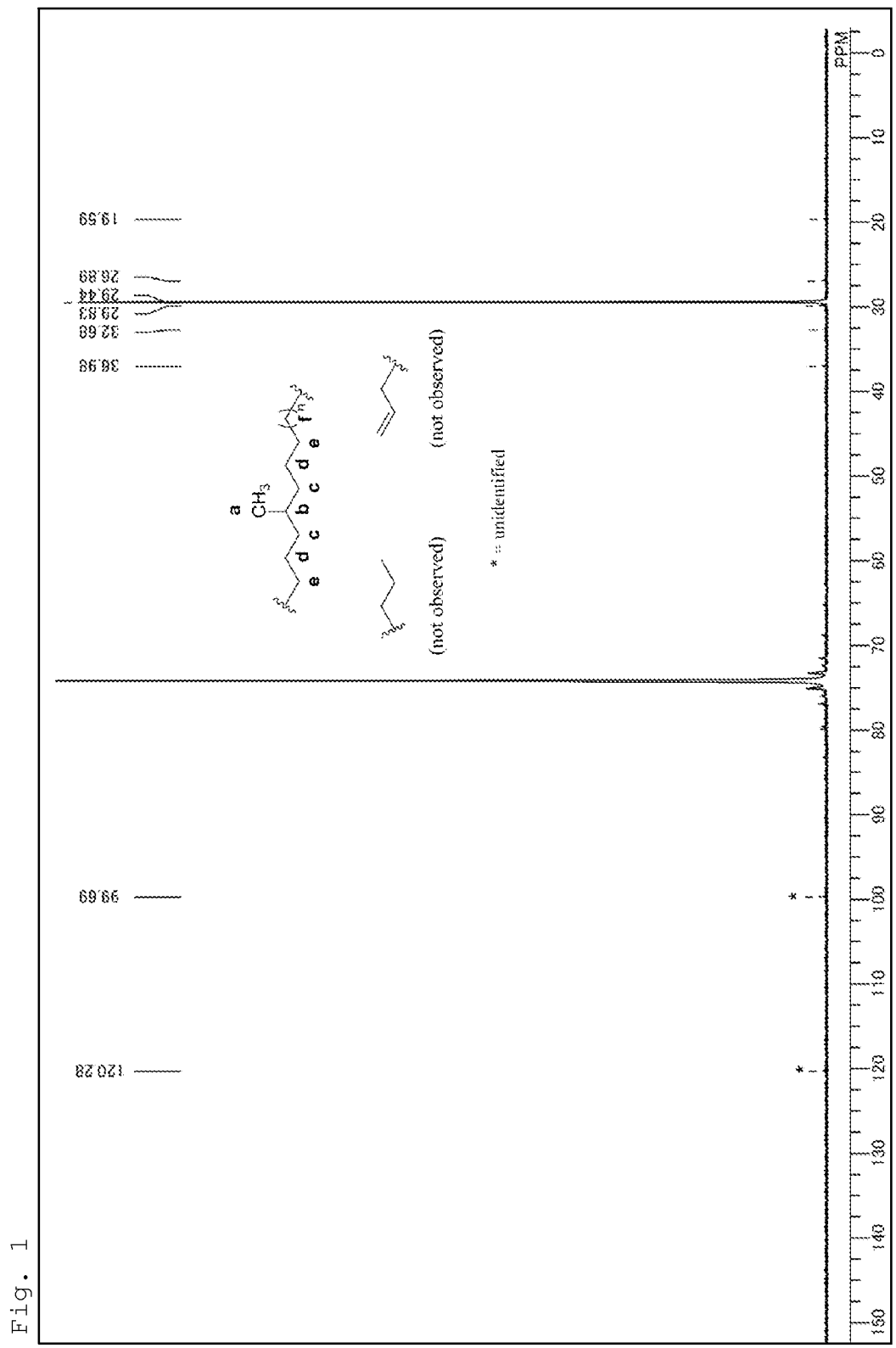
FIG. 1 $^{13}$C-NMR chart of the product of Example 5
FIG. 2 $^{13}$C-NMR chart of the product of Example 10
FIG. 3 $^{13}$C-NMR chart of the product of Example 12
FIG. 4 $^{13}$C-NMR chart of the product of Example 14
FIG. 5 $^{13}$C-NMR chart of the product of Example 16
FIG. 6 $^{13}$C-NMR chart of the product of Example 18

The organometallic compound of the present invention is a compound comprising a complex formed by bisphosphine monoxide (BPMO) represented by formula (I) as a ligand with metal center M composed of an element belonging to Group 10 in the periodic system.

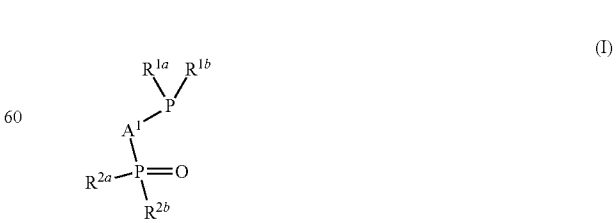

(I)

Here, M represents an element belonging to Group 10 in the periodic system.

In formula (I), $R^{1a}$, $R^{1b}$, $R^{2a}$, and $R^{2b}$ may be the same or different with each other and independently represent substituted or unsubstituted alkyl group having 1 to 14 carbon atoms, substituted or unsubstituted cycloalkyl group having 3 to 14 carbon atoms, substituted or unsubstituted biphenyl group ($C_6H_5$—$C_6H_4$—) or substituted or unsubstituted aryl group; and preferably substituted or unsubstituted alkyl group having 1 to 14 carbon atoms.

Also, a pair of $R^{1a}$ and $R^{1b}$ and a pair of $R^{2a}$ and $R^{2b}$ may be bonded and form a ring structure.

Specific examples of the [($R^{1a}$)($R^{1b}$)P] and [($R^{2a}$)($R^{2b}$)P] sites include the following structures. In the following structure formulae, the bonds between P and O, and P and $A^1$ are omitted.

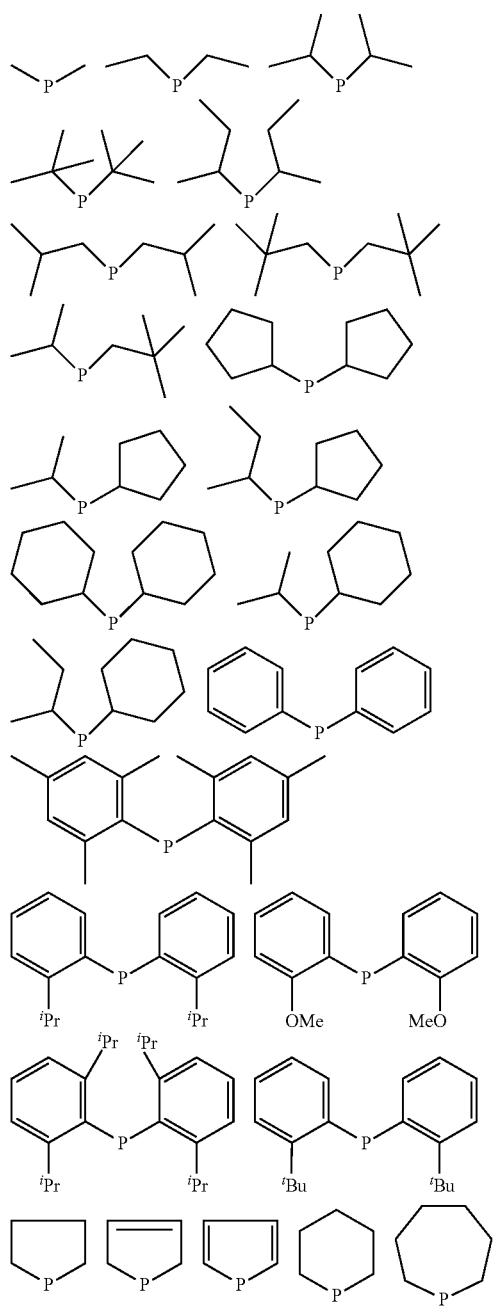

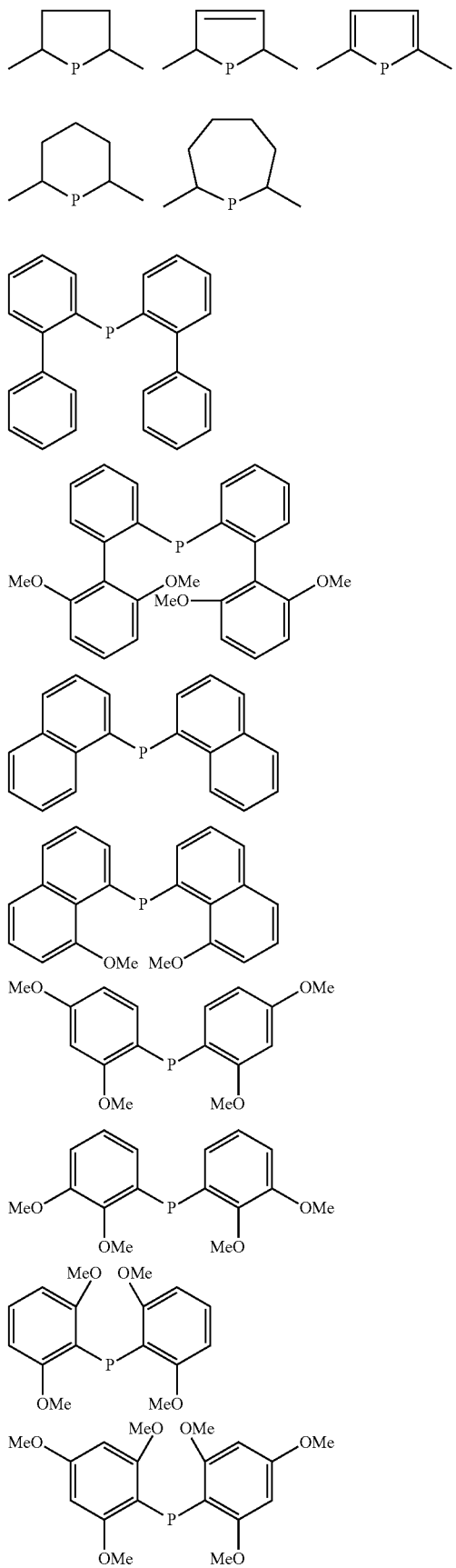

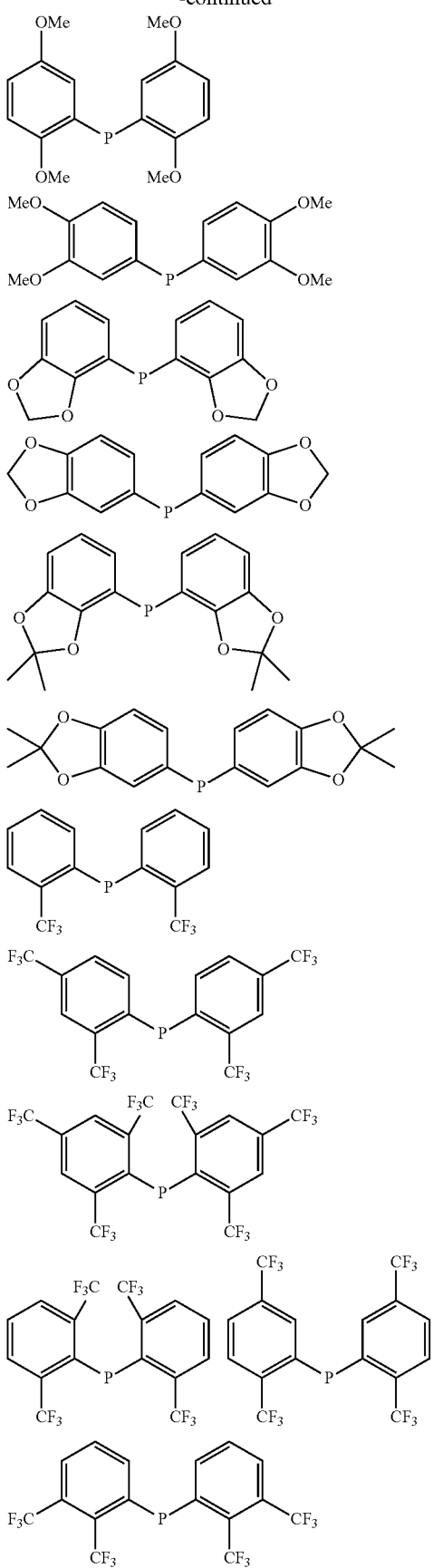

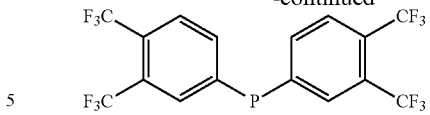

$A^1$ represents an arylene group, a monocyclic heteroarylene group, bivalent heterocyclic group, alkylene group having 1 to 2 carbon atoms, cycloalkylene group having 3 to 10 carbon atoms, alkenylene group having 2 to 8 carbon group, or cycloalkenylene group having 3 to 10 carbon atoms. Examples of $A^1$ include ortho-phenylene group, 1,2-naphthylene group, 1,8-naphthylene group, 1,2-cyclohexylene group, 1,2-cyclopentylene group, 1,2-vinylene group, 1,2-cyclohexenylene group, 1,2-cyclopentenylene group, methylene group, and ethylene group which is unsubstituted or in which alkyl group, alkoxy group, amino group or ester group may be substituted. From the viewpoint of the ease of synthesis, ortho-phenylene group, 1,2-naphthylene group, 1,8-naphthylene group and methylene group are preferable, and ortho-phenylene group and methylene group are more preferable.

One embodiment of the present invention is an organometallic compound represented by formula (II).

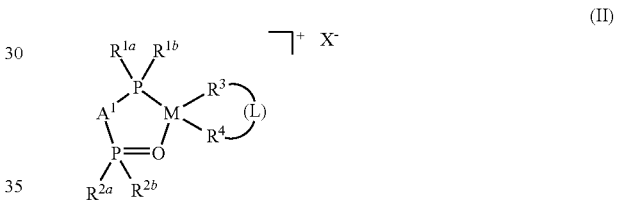

(II)

In formula (II), M, $R^{1a}$, $R^{1b}$, $R^{2a}$, $R^{2b}$ and $A^1$ have the meanings as described above.

$R^3$ represents alkyl group having 1 to 10 carbon atoms, alkenyl group having 1 to 10 carbon atoms or bivalent group represented by $A^2$; and $A^2$ represents arylene group, monocyclic heteroarylene group, monocyclic cycloalkylene group, monocyclic cycloalkenylene group, monocyclic heterocycloalkylene group, monocyclic heterocycloalkenylene group, or heterocyclic or C2-C4 alkylene group.

$R^4$ represents a neutral electron-donating ligand. Examples of a neutral electron-donating ligand include pyridine, substituted pyridine, quinoline, substituted quinoline, nitrile compounds, ammonia, alkylamine, substituted alkylamine, arylamine, substituted arylamine, sulfoxide, alkylphosphine, substituted alkylphosphine, arylphosphine, substituted arylphosphine, alkyl phosphite, substituted alkyl phosphite, aryl phosphite, substituted aryl phosphite, aliphatic ether, substituted aliphatic ether, cyclic ether, and substituted cyclic ether. Specifically, pyridine, 2,6-dimethylpyridine, 4-(N,N-dimethylamino)pyridine (DMAP); quinoline, 2-methylquinoline; trialkylamine having 1 to 10 carbon atoms, N,N,N',N'-tetramethylethylenediamine (TMEDA); dialkylaminoaniline, 2,6-dimethylaniline, 2,6-diisopropylaniline, acetonitrile, benzonitrile; dimethylsulfoxide (DMSO); trimethylphosphine, triisopropylphosphine, tributylphosphine, tri(t-butyl)phosphine, triphenylphosphine, tris(o-tolyl)phosphine, trifurylphosphine; diethyl ether; tetrahydrofuran, 1,4-dioxane; and 1,2-dimethoxyethane.

In another embodiment of the present invention, $R^4$ is selected from pyridine, substituted pyridine, nitrile compounds, ammonia, alkylamine, substituted alkylamine, arylamine and substituted arylamine; and preferably pyridine or substituted pyridine.

In another embodiment of the present invention, ligand $R^4$ is represented by formula (1).

In formula (1), W represents a carbon atom (C) or a sulfur atom (S), Z is selected from an oxygen atom (O), S, NH or $NR^a$ ($R^a$ represents alkyl group or aryl group); Y is selected from O, S, NH or $NR^b$ ($R^b$ represents alkyl group or aryl group); $R^5$ is substituted or unsubstituted alkyl group having 1 to 10 carbon atoms, $OR^c$ ($R^c$ represents alkyl group or aryl group) or $NR^d_2$ ($R^d$ represents alkyl group or aryl group).

$R^3$ and $R^4$ may be crosslinked, and when $R^3$ and $R^4$ are crosslinked, L represents a single bond or bivalent group selected from alkylene group, haloalkylene group, alkenylene group and alkynylene group. When $R^3$ and $R^4$ are not crosslinked, L does not exist.

$R^4$ needs not exist. When $R^4$ does not exist, the embodiment of the organometallic compound represented by formula (II) becomes the threefold-coordination organometallic compound represented by formula (IIa).

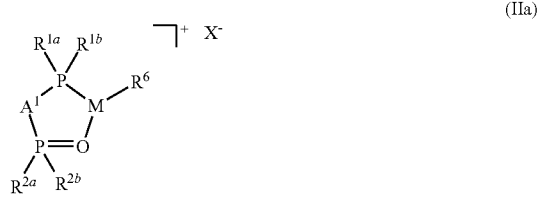

In the formula, M, $R^{1a}$, $R^{1b}$, $R^{2a}$, $R^{2b}$ and $A^1$ have the meanings as described above.

$X^-$ represents a counterion of the cationic organometallic complex. The counterion represented by X– may be any monovalent anion. Further, if the charge number per atom of the metal center (M) is monovalent, $X^-$ may be a polyvalent anion. Specifically, examples include sulfate ion ($SO_4^{2-}$), nitrate ion ($NO_3^-$), carbonate ion ($CO_3^{2-}$), perchlorate ion ($ClO_4^-$), halide ion such as chloride ion ($Cl^-$), bromide ion ($Br^-$) and iodide ion ($I^-$); borate ion such as tetrafluoroborate ($BF_4^-$), bromotrifluoroborate ($BBrF_3^-$), chlorotrifluoroborate ($BClF_3^-$), trifluoromethoxyborate ($BF_3(OCH_3)^-$), trifluoroethoxyborate ($BF_3(OC_2H_5)^-$), trifluoroallyloxyborate ($BF_3(OC_3H_5)^-$), tetraphenylborate ($B(C_6H_5)_4^-$), tetrakis(3,5-bis(trifluoromethyl)phenyl)borate ($B(3,5-(CF_3)_2C_6H_3)_4^- = BArF_4^-$), bromotriphenylborate ($BBr(C_6H_5)_3^-$), chlorotriphenylborate ($BCl(C_6H_5)_3^-$), methoxytriphenylborate ($B(OCH_3)(C_6H_5)_3^-$), ethoxytriphenylborate ($B(OC_2H_5)(C_6H_5)_3^-$), allyloxytriphenylborate ($B(OC_3H_5)(C_6H_5)_3^-$), tetrakis(pentafluorophenyl)borate ($B(C_6F_5)_4^-$), bromotris(pentafluorophenyl)borate ($BBr(C_6F_5)_3^-$), chlorotris(pentafluorophenyl)borate ($BCl(C_6F_5)_3^-$), methoxytris(pentafluorophenyl)borate ($B(OCH_3)(C_6F_5)_3^-$), ethoxytris(pentafluorophenyl)borate ($B(OC_2H_5)(C_6F_5)_3^-$) and allyloxytris(pentafluorophenyl)borate ($B(OC_3H_5)(C_6F_5)_3^-$); sulfonate ion such as methanesulfonate ion ($CH_3SO_3^-$), trifluoromethanesulfonate ($CF_3SO_3^-$), nonafluorobutanesulfonate ($C_4F_9SO_3^-$), benzenesulfonate ($C_6H_5SO_3^-$) and p-toluenesulfonate (p-$CH_3$—$C_6H_4SO_3^-$); carboxylate ion such as acetate ion ($CH_3CO_2^-$), trifluoroacetate ion ($CF_3CO_2^-$), trichloroacetate ion ($CCl_3CO_2^-$), propionate ion ($C_2H_5CO_2$—) and benzoate ion ($C_6H_5CO_2^-$); phosphate ion such as hexafluorophosphate ion ($PF_6^-$); arsenate ion such as hexafluoroarsenate ion ($AsF_6^-$); antimonate ion such as hexafluoroantimonate ($SbF_6^-$); and silicate ion such as hexafluorosilicate ($SiF_6^-$). Among these counterions, preferred are those in which $X^-$ is $SbF_6^-$, $BPh_4^-$, $BArF_4^-$, $BF_4^-$ and $PF_6^-$.

Among the organometallic compounds represented by formula (II) of the present invention, a preferred embodiment is an organometallic compound represented by formula (III).

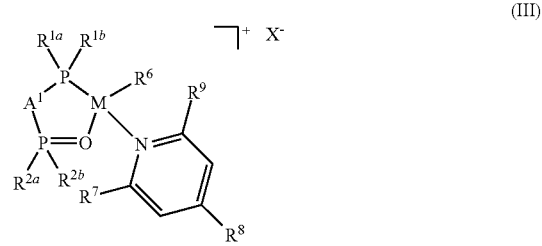

In formula (III), M, $R^{1a}$, $R^{1b}$, $R^{2a}$, $R^{2b}$, $A^1$ and $X^-$ have the meanings as described above.

$R^6$ represents an alkyl group, alkenyl group or aryl group, which has 1 to 10 carbon atoms.

$R^7$, $R^8$ and $R^9$ independently represent a hydrogen atom, or alkyl group or alkoxy group, which has 1 to 4 carbon atoms.

In formula (III), $A^1$ is preferably a substituted or unsubstituted phenylene group, substituted or unsubstituted naphthylene group, or substituted or unsubstituted methylene group.

Among the organometallic compounds represented by formula (III) of the present invention, a preferred embodiment is an organometallic compound represented by the following formula (IIIa).

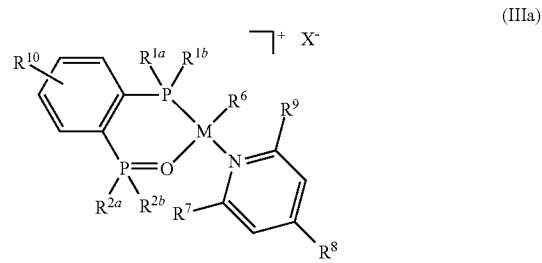

Here, M, $R^{1a}$, $R^{1b}$, $R^{2a}$, $R^{2b}$, $R^7$, $R^8$, $R^9$ and $X^-$ have the meanings as described above.

$R^{10}$ does not exist, or represents an alkyl group having 1 to 10 carbon atoms, which is substituted with an arbitrary replaceable hydrogen in a benzene ring, and when two or more $R^{10}$'s exist, they may be the same or different with each other.

Meanwhile, an organometallic compound represented by formula (IIIc) is a preferred embodiment among the organometallic compounds represented by formula (III) as well.

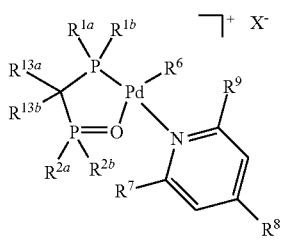

(IIIc)

In the formula, $R^{1a}$, $R^{1b}$, $R^{2a}$, $R^{2b}$, $R^7$, $R^8$, $R^9$ and $X^-$ have the meanings as described above.

$R^{13a}$ and $R^{13b}$ independently represent a hydrogen atom, alkyl group having 1 to 10 carbon atoms or aryl group having 6 to 12 carbon atoms, and may be the same or different with each other. $R^{13a}$ and $R^{13b}$ may bond to each other to form a crosslinked structure.

In formulae (III), (IIIa) or (IIIc), $R^{1a}$, $R^{1b}$, $R^{2a}$ and $R^{2b}$, independently from each other, are preferably a substituted or unsubstituted alkyl group having 1 to 14 carbon atoms, and more preferably, a branched alkyl group having 3 to 5 carbon atoms. In a conventional transition metal complex to which phosphine-sulfonate is coordinated, an aryl group have been used as a substituent of a phosphorus atom. In a novel organometallic compound of the present invention to which bis-phosphine monoxide (BPMO) is coordinated, it was found that the compound exhibited higher activity in polymerization of olefins when an alkyl group was used as a substituent of a phosphorus atom than the case where an aryl group was used.

In the present invention, it is especially preferable that $R^{1a}$, $R^{1b}$, $R^{2a}$ and $R^{2b}$ in formula (III) are an isopropyl group or t-butyl group, independently from each other. It is particularly preferable that $R^{1a}$ and $R^{1b}$ are an isopropyl group and $R^{2a}$ and $R^{2b}$ are a t-butyl group.

In an embodiment where the organometallic compound of the present invention is a compound represented by formula (IIIc), both of R13a and R13b in formula (IIIc) are preferably a hydrogen atom or a methyl group, more preferably a hydrogen atom.

In formula (III), M is an element belonging to Group 10 in the periodic system, preferably nickel or palladium, and more preferably, palladium.

Among the organometallic compounds represented by formula (II) of the present invention, another preferred embodiment is an organometallic compound represented by formula (IV).

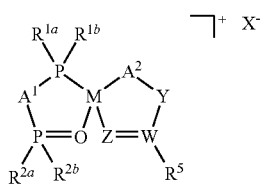

(IV)

In formula (IV), M, $R^{1a}$, $R^{1b}$, $R^{2a}$, $R^{2b}$, $A^1$ and $X^-$ have the meanings as described above.

In the organometallic compound of formula (IV), the portion represented by formula (1) forms a closed ring structure within a molecule. Here, a conventional transition metal complex to which phosphine-sulfonate is coordinated was stabilized using strong Lewis base such as pyridine, but it tended to inhibit vinyl monomer from inserting/coordinating to the metal. In the novel organometallic compound represented by formula (IV), introducing weak Lewis base as "Z" can stabilize the complex by forming a closed ring structure within a molecule, as well as facilitate the insertion/coordination of the vinyl monomer to the metal.

Here, as defined in formula (1), W represents C or S; Z is selected from O, S, NH or $NR^a$ ($R^a$ represents alkyl group or aryl group) and when Y exists, Y is selected from O, S, NH or $NR^b$ ($R^b$ represents alkyl group or aryl group); $R^5$ represents a substituted or unsubstituted alkyl group having 1 to 10 carbon atoms, $OR^c$ ($R^c$ represents alkyl group or aryl group), $NR^d_2$ or $SR^d$ ($R^d$ represents alkyl group or aryl group). When Y does not exist, W is directly bonded to $A^2$. Specific examples of ligands represented by YW(=Z)$R^5$ (1) include OC(=O)R, OC(=O)OR, NHC(=O)R, NHC(=O)OR, C(=O)OR, OC(=S)R, OC(=S)SR, C(=O)NHR, C(=O)N(R)$_2$ and OS(=O)OR(R represents an alkyl or aryl group, and when two R's exist, they may be the same or different).

In one preferred embodiment of the present invention, the organometallic compound is represented by formula (IVa) in which the ligand represented by YW(=Z)$R^5$ (1) is NH(C=O)$R^5$.

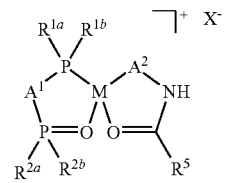

(IVa)

In the formula, M, $R^{1a}$, $R^{1b}$, $R^{2a}$, $R^{2b}$, $R^5$, $A^1$, $A^2$ and $X^-$ have the same meanings as described above.

$A^2$ represents arylene group, monocyclic heteroarylene group, monocyclic cycloalkylene group, monocyclic cycloalkenylene group, monocyclic heterocycloalkylene group, monocyclic heterocycloalkenylene group, heterocyclic group or C2-C4 alkylene group. Specifically, examples of $A^2$ include o-phenylene group, 1,2-naphthylene group, 1,8-naphthylene group, 1,2-cyclohexylene group, 1,2-cyclopentylene group; ethylene group (—CH$_2$—CH$_2$—), propylene group (—CH$_2$—CH$_2$—CH$_2$—) and butylene group (—CH$_2$—CH$_2$—CH$_2$—CH$_2$—) group, which are unsubstituted, or wherein alkyl group, alkoxy group, amino group, ester group may be substituted.

In formula (IV), $A^1$ represents arylene group, monocyclic heteroarylene group, heterocyclic group, alkylene group having 1 to 2 carbon atoms, cycloalkylene group having 3 to 10 carbon atoms, alkenylene group having 2 to 8 carbon atoms, or cycloalkenylene group having 3 to 10 carbon atoms. Preferred are substituted or unsubstituted phenylene group, substituted or unsubstituted naphthylene group, or substituted or unsubstituted methylene group.

Among the organometallic compounds represented by formula (IV) of the present invention, one preferred embodiment is an organometallic compound represented by formula (V).

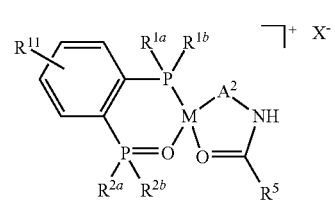

(V)

In formula (V), M, $R^{1a}$, $R^{1b}$, $R^{2a}$, $R^{2b}$, $A^2$, $R^5$ and $X^-$ have the same meanings as described above.

$R^{11}$ does not exist, or represents an alkyl group having 1 to 10 carbon atoms, which is substituted with an arbitrary replaceable hydrogen in a benzene ring, and when two or more $R^{11}$'s exist, they may be the same or different with each other.

In formula (V), $A^2$ represents arylene group, monocyclic heteroarylene group, monocyclic cycloalkylene group, monocyclic cycloalkenylene group, monocyclic heterocycloalkylene group, monocyclic heterocycloalkenylene group, or heterocyclic or C2-C4 alkylene group. Preferred are substituted or unsubstituted phenylene group and substituted or unsubstituted naphthylene group.

Among the organometallic compounds represented by formula (IV) of the present invention, another preferred embodiment is the organometallic compound represented by the following formula (VI).

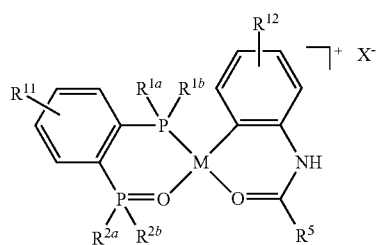

(VI)

In formula (VI), M, $R^{1a}$, $R^{1b}$, $R^{2a}$, $R^{2b}$, $R^5$, $R^{11}$ and $X^-$ have the same meanings as described above.

$R^{12}$ does not exist, or represents an alkyl group having 1 to 10 carbon atoms, which is substituted with an arbitrary replaceable hydrogen in a benzene ring, and when two or more $R^{12}$'s exist, they may be the same or different with each other.

In formulae (IV) to (VI), $R^{1a}$, $R^{1b}$, $R^{2a}$ and $R^{2b}$, independently from each other, are preferably substituted or unsubstituted alkyl group having 1 to 10 carbon atoms, more preferably a branched alkyl group having 3 to 5 carbon atoms. It is preferable that $R^{1a}$, $R^{1b}$, $R^{2a}$ and $R^{2b}$ are an isopropyl group or t-butyl group, independently from each other. It is particularly preferable that $R^{1a}$ and $R^{1b}$ are an isopropyl group and $R^{2a}$ and $R^{2b}$ are a t-butyl group.

In formulae (IV) to (VI), M is an element belonging to Group 10 in the periodic system and preferably nickel or palladium, more preferably, palladium.

An example of the organometallic compounds represented by formula (III) of the present invention, wherein $A^1$ is phenylene, can be synthesized, for example, by the following scheme 1.

Scheme 1

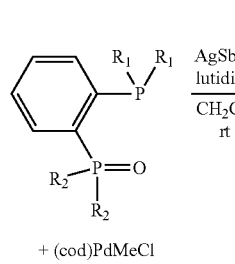

+ (cod)PdMeCl

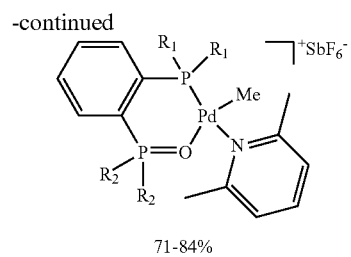

71-84%

The compound can be obtained by, after mixing free bisphosphine monoxide (BPMO) and (cod)PdMeCl (cod=1,5-cyclooctadiene), treating the intermediate (BPMO)(cod)PdMeCl complex with silver hexafluoroantimonate and 2,6-lutidine.

Specific examples of the organometallic compounds represented by formulae (II) to (VI) of the present invention are described below.

Regarding the case where $R^{10}$ does not exist in formula (IIIa) (i.e. where there is no substituent of $R^{10}$ in a benzene ring), specific examples of the organometallic compounds represented by the following formula (IIIb) of the present invention are shown in Table I.

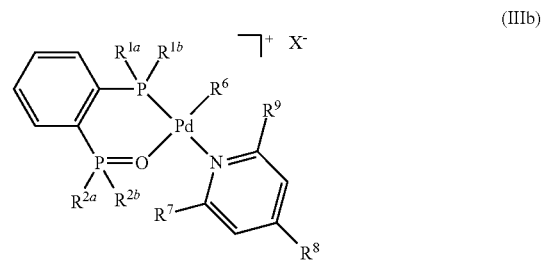

(IIIb)

In Table I, H represents a hydrogen atom, Me represents a methyl group, Et represents an ethyl group, n-Pr represents an n-propyl group, i-Pr represents an isopropyl group, tert-Bu represents a t-butyl group, NeoPen represents a neopentyl group, CyHex represents a cyclohexyl group, CyPen represents a cyclopentyl group, 1-Ada represents a 1-adamantyl group, and Biph represents 2'-[2,6-bis(dimethoxy)]biphenyl group. HIPT represents a group represented by the following formula.

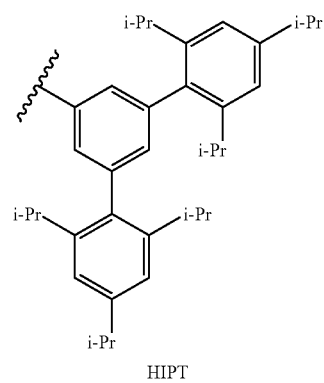

HIPT

TABLE I

| Compound No. | R 1a | 1b | 2a | 2b | 6 | 7 | 8 | 9 | X |
|---|---|---|---|---|---|---|---|---|---|
| 1 | i-Pr | i-Pr | i-Pr | i-Pr | Me | H | H | H | SbF$_6$ |
| 2 | i-Pr | i-Pr | i-Pr | i-Pr | Me | Me | Me | H | SbF$_6$ |
| 3 | i-Pr | i-Pr | i-Pr | i-Pr | Me | Me | Me | Me | SbF$_6$ |
| 4 | i-Pr | i-Pr | i-Pr | i-Pr | Me | Me | H | Me | SbF$_6$ |
| 5 | i-Pr | tert-Bu | i-Pr | i-Pr | Me | H | H | H | SbF$_6$ |
| 6 | i-Pr | i-Pr | tert-Bu | i-Pr | Me | H | H | H | SbF$_6$ |
| 7 | i-Pr | tert-Bu | i-Pr | tert-Bu | Me | H | H | H | SbF$_6$ |
| 8 | i-Pr | i-Pr | tert-Bu | tert-Bu | Me | H | H | H | SbF$_6$ |
| 9 | i-Pr | i-Pr | tert-Bu | tert-Bu | Me | Me | Me | H | SbF$_6$ |
| 10 | i-Pr | i-Pr | tert-Bu | tert-Bu | Me | Me | Me | Me | SbF$_6$ |
| 11 | i-Pr | i-Pr | tert-Bu | tert-Bu | Me | Me | H | Me | SbF$_6$ |
| 12 | i-Pr | i-Pr | NeoPen | NeoPen | Me | H | H | H | SbF$_6$ |
| 13 | i-Pr | i-Pr | NeoPen | NeoPen | Me | Me | H | Me | SbF$_6$ |
| 14 | i-Pr | i-Pr | NeoPen | NeoPen | Me | Me | Me | Me | SbF$_6$ |
| 15 | i-Pr | i-Pr | NeoPen | NeoPen | Me | Me | H | Me | SbF$_6$ |
| 16 | i-Pr | i-Pr | CyHex | CyHex | Me | H | H | H | SbF$_6$ |
| 17 | i-Pr | i-Pr | CyHex | CyHex | Me | Me | H | Me | SbF$_6$ |
| 18 | i-Pr | i-Pr | CyPen | CyPen | Me | H | H | H | SbF$_6$ |
| 19 | i-Pr | i-Pr | CyPen | CyPen | Me | Me | H | Me | SbF$_6$ |
| 20 | i-Pr | i-Pr | Me | Me | Me | H | H | H | SbF$_6$ |
| 21 | i-Pr | i-Pr | Me | Me | Me | Me | Me | H | SbF$_6$ |
| 22 | i-Pr | i-Pr | Me | Me | Me | Me | Me | Me | SbF$_6$ |
| 23 | i-Pr | i-Pr | Me | Me | Me | Me | H | Me | SbF$_6$ |
| 24 | i-Pr | i-Pr | Et | Et | Me | H | H | H | SbF$_6$ |
| 25 | i-Pr | i-Pr | Et | Et | Me | Me | H | Me | SbF$_6$ |
| 26 | i-Pr | i-Pr | n-Pr | n-Pr | Me | H | H | H | SbF$_6$ |
| 27 | i-Pr | i-Pr | n-Pr | n-Pr | Me | Me | H | Me | SbF$_6$ |
| 28 | tert-Bu | tert-Bu | i-Pr | i-Pr | Me | H | H | H | SbF$_6$ |
| 29 | tert-Bu | tert-Bu | i-Pr | i-Pr | Me | Me | Me | H | SbF$_6$ |
| 30 | tert-Bu | tert-Bu | i-Pr | i-Pr | Me | Me | Me | Me | SbF$_6$ |
| 31 | tert-Bu | tert-Bu | i-Pr | i-Pr | Me | Me | H | Me | SbF$_6$ |
| 32 | tert-Bu | tert-Bu | tert-Bu | tert-Bu | Me | H | H | H | SbF$_6$ |
| 33 | tert-Bu | tert-Bu | tert-Bu | tert-Bu | Me | Me | Me | H | SbF$_6$ |
| 34 | tert-Bu | tert-Bu | tert-Bu | tert-Bu | Me | Me | Me | Me | SbF$_6$ |
| 35 | tert-Bu | tert-Bu | tert-Bu | tert-Bu | Me | Me | H | Me | SbF$_6$ |
| 36 | tert-Bu | tert-Bu | tert-Bu | i-Pro | Me | H | H | H | SbF$_6$ |
| 37 | tert-Bu | tert-Bu | NeoPen | NeoPen | Me | H | H | H | SbF$_6$ |
| 38 | tert-Bu | tert-Bu | NeoPen | NeoPen | Me | Me | H | Me | SbF$_6$ |
| 39 | tert-Bu | tert-Bu | NeoPen | NeoPen | Me | Me | Me | Me | SbF$_6$ |
| 40 | tert-Bu | tert-Bu | NeoPen | NeoPen | Me | Me | H | Me | SbF$_6$ |
| 41 | tert-Bu | tert-Bu | CyHex | CyHex | Me | H | H | H | SbF$_6$ |
| 42 | tert-Bu | tert-Bu | CyHex | CyHex | Me | Me | H | Me | SbF$_6$ |
| 43 | tert-Bu | tert-Bu | CyPen | CyPen | Me | H | H | H | SbF$_6$ |
| 44 | tert-Bu | tert-Bu | CyPen | CyPen | Me | Me | H | Me | SbF$_6$ |
| 45 | tert-Bu | tert-Bu | Me | Me | Me | H | H | H | SbF$_6$ |
| 46 | tert-Bu | tert-Bu | Me | Me | Me | Me | H | Me | SbF$_6$ |
| 47 | tert-Bu | tert-Bu | Et | Et | Me | H | H | H | SbF$_6$ |
| 48 | tert-Bu | tert-Bu | Et | Et | Me | Me | H | Me | SbF$_6$ |
| 49 | tert-Bu | tert-Bu | n-Pr | n-Pr | Me | H | H | H | SbF$_6$ |
| 50 | tert-Bu | tert-Bu | n-Pr | n-Pr | Me | Me | H | Me | SbF$_6$ |
| 51 | NeoPen | NeoPen | i-Pr | i-Pr | Me | H | H | H | SbF$_6$ |
| 52 | NeoPen | NeoPen | i-Pr | i-Pr | Me | Me | H | Me | SbF$_6$ |
| 53 | NeoPen | NeoPen | tert-Bu | tert-Bu | Me | H | H | H | SbF$_6$ |
| 54 | NeoPen | NeoPen | tert-Bu | tert-Bu | Me | Me | H | Me | SbF$_6$ |
| 55 | NeoPen | NeoPen | NeoPen | NeoPen | Me | H | H | H | SbF$_6$ |
| 56 | NeoPen | NeoPen | NeoPen | NeoPen | Me | Me | H | Me | SbF$_6$ |
| 57 | NeoPen | NeoPen | CyHex | CyHex | Me | H | H | H | SbF$_6$ |
| 58 | NeoPen | NeoPen | Me | Me | Me | Me | H | Me | SbF$_6$ |
| 59 | NeoPen | NeoPen | Et | Et | Me | Me | H | Me | SbF$_6$ |
| 60 | NeoPen | NeoPen | n-Pr | n-Pr | Me | Me | H | Me | SbF$_6$ |
| 61 | CyHex | CyHex | i-Pr | i-Pr | Me | Me | H | Me | SbF$_6$ |
| 62 | CyHex | CyHex | tert-Bu | tert-Bu | Me | Me | H | Me | SbF$_6$ |
| 63 | CyHex | CyHex | Me | Me | Me | Me | H | Me | SbF$_6$ |
| 64 | CyHex | CyHex | Et | Et | Me | Me | H | Me | SbF$_6$ |
| 65 | CyHex | CyHex | n-Pr | n-Pr | Me | Me | H | Me | SbF$_6$ |
| 66 | CyPen | CyPen | i-Pr | i-Pr | Me | Me | H | Me | SbF$_6$ |
| 67 | CyPen | CyPen | tert-Bu | tert-Bu | Me | Me | H | Me | SbF$_6$ |
| 68 | CyPen | CyPen | Me | Me | Me | Me | H | Me | SbF$_6$ |
| 69 | CyPen | CyPen | Et | Et | Me | Me | H | Me | SbF$_6$ |
| 70 | Me | Me | i-Pr | i-Pr | Me | Me | H | Me | SbF$_6$ |
| 71 | Me | Me | tert-Bu | tert-Bu | Me | Me | H | Me | SbF$_6$ |
| 72 | Me | Me | NeoPen | NeoPen | Me | Me | H | Me | SbF$_6$ |
| 73 | Me | Me | CyHex | CyHex | Me | Me | H | Me | SbF$_6$ |
| 74 | Me | Me | Et | Et | Me | Me | H | Me | SbF$_6$ |
| 75 | Me | Me | n-Pr | n-Pr | Me | Me | H | Me | SbF$_6$ |
| 76 | Et | Et | i-Pr | i-Pr | Me | Me | H | Me | SbF$_6$ |

TABLE I-continued

| Compound No. | R | | | | | | | | |
|---|---|---|---|---|---|---|---|---|---|
| | 1a | 1b | 2a | 2b | 6 | 7 | 8 | 9 | X |
| 77 | Et | Et | tert-Bu | tert-Bu | Me | Me | H | Me | SbF$_6$ |
| 78 | Et | Et | NeoPen | NeoPen | Me | Me | H | Me | SbF$_6$ |
| 79 | Et | Et | CyHex | CyHex | Me | Me | H | Me | SbF$_6$ |
| 80 | Et | Et | n-Pr | n-Pr | Me | Me | H | Me | SbF$_6$ |
| 81 | Et | Et | Me | Me | Me | Me | H | Me | SbF$_6$ |
| 82 | n-Pr | n-Pr | i-Pr | i-Pr | Me | Me | H | Me | SbF$_6$ |
| 83 | n-Pr | n-Pr | tert-Bu | tert-Bu | Me | Me | H | Me | SbF$_6$ |
| 84 | n-Pr | n-Pr | NeoPen | NeoPen | Me | Me | H | Me | SbF$_6$ |
| 85 | n-Pr | n-Pr | CyHex | CyHex | Me | Me | H | Me | SbF$_6$ |
| 86 | n-Pr | n-Pr | Me | Me | Me | Me | H | Me | SbF$_6$ |
| 87 | 1-Ada | 1-Ada | i-Pr | i-Pr | Me | Me | H | Me | SbF$_6$ |
| 88 | 1-Ada | 1-Ada | tert-Bu | tert-Bu | Me | Me | H | Me | SbF$_6$ |
| 89 | 1-Ada | 1-Ada | NeoPen | NeoPen | Me | Me | H | Me | SbF$_6$ |
| 90 | 1-Ada | 1-Ada | Me | Me | Me | Me | H | Me | SbF$_6$ |
| 91 | 1-Ada | 1-Ada | Et | Et | Me | Me | H | Me | SbF$_6$ |
| 92 | 1-Ada | 1-Ada | n-Pr | n-Pr | Me | Me | H | Me | SbF$_6$ |
| 93 | HIPT | HIPT | i-Pr | i-Pr | Me | Me | H | Me | SbF$_6$ |
| 94 | HIPT | HIPT | tert-Bu | tert-Bu | Me | Me | H | Me | SbF$_6$ |
| 95 | HIPT | HIPT | NeoPen | NeoPen | Me | Me | H | Me | SbF$_6$ |
| 96 | HIPT | HIPT | Me | Me | Me | Me | H | Me | SbF$_6$ |
| 97 | HIPT | HIPT | Et | Et | Me | Me | H | Me | SbF$_6$ |
| 98 | HIPT | HIPT | n-Pr | n-Pr | Me | Me | H | Me | SbF$_6$ |
| 99 | Biph | Biph | i-Pr | i-Pr | Me | Me | H | Me | SbF$_6$ |
| 100 | Biph | Biph | tert-Bu | tert-Bu | Me | Me | H | Me | SbF$_6$ |
| 101 | Biph | Biph | NeoPen | NeoPen | Me | Me | H | Me | SbF$_6$ |
| 102 | Biph | Biph | Me | Me | Me | Me | H | Me | SbF$_6$ |
| 103 | i-Pr | i-Pr | i-Pr | i-Pr | Me | Me | H | Me | BArF$_4$ |
| 104 | i-Pr | tert-Bu | i-Pr | i-Pr | Me | Me | H | Me | BArF$_4$ |
| 105 | i-Pr | i-Pr | tert-Bu | i-Pr | Me | Me | H | Me | BArF$_4$ |
| 106 | i-Pr | tert-Bu | i-Pr | tert-Bu | Me | Me | H | Me | BArF$_4$ |
| 107 | i-Pr | i-Pr | tert-Bu | tert-Bu | Me | Me | H | Me | BArF$_4$ |
| 108 | i-Pr | i-Pr | NeoPen | NeoPen | Me | Me | H | Me | BArF$_4$ |
| 109 | i-Pr | i-Pr | CyHex | CyHex | Me | Me | H | Me | BArF$_4$ |
| 110 | i-Pr | i-Pr | Me | Me | Me | Me | H | Me | BArF$_4$ |
| 111 | i-Pr | i-Pr | Et | Et | Me | Me | H | Me | BArF$_4$ |
| 112 | tert-Bu | tert-Bu | i-Pr | i-Pr | Me | Me | H | Me | BArF$_4$ |
| 113 | tert-Bu | tert-Bu | tert-Bu | tert-Bu | Me | Me | H | Me | BArF$_4$ |
| 114 | tert-Bu | tert-Bu | NeoPen | NeoPen | Me | Me | H | Me | BArF$_4$ |
| 115 | tert-Bu | tert-Bu | CyHex | CyHex | Me | Me | H | Me | BArF$_4$ |
| 116 | tert-Bu | tert-Bu | Me | Me | Me | Me | H | Me | BArF$_4$ |
| 117 | tert-Bu | tert-Bu | Et | Et | Me | Me | H | Me | BArF$_4$ |
| 118 | tert-Bu | tert-Bu | n-Pr | n-Pr | Me | Me | H | Me | BArF$_4$ |
| 119 | NeoPen | NeoPen | i-Pr | i-Pr | Me | Me | H | Me | BArF$_4$ |
| 120 | NeoPen | NeoPen | tert-Bu | tert-Bu | Me | Me | H | Me | BArF$_4$ |
| 121 | NeoPen | NeoPen | NeoPen | NeoPen | Me | Me | H | Me | BArF$_4$ |
| 122 | NeoPen | NeoPen | CyHex | CyHex | Me | Me | H | Me | BArF$_4$ |
| 123 | NeoPen | NeoPen | Me | Me | Me | Me | H | Me | BArF$_4$ |
| 124 | CyHex | CyHex | i-Pr | i-Pr | Me | Me | H | Me | BArF$_4$ |
| 125 | CyHex | CyHex | tert-Bu | tert-Bu | Me | Me | H | Me | BArF$_4$ |
| 126 | CyPen | CyPen | i-Pr | i-Pr | Me | Me | H | Me | BArF$_4$ |
| 127 | CyPen | CyPen | tert-Bu | tert-Bu | Me | Me | H | Me | BArF$_4$ |
| 128 | Me | Me | i-Pr | i-Pr | Me | Me | H | Me | BArF$_4$ |
| 129 | Me | Me | tert-Bu | tert-Bu | Me | Me | H | Me | BArF$_4$ |
| 130 | Et | Et | i-Pr | i-Pr | Me | Me | H | Me | BArF$_4$ |
| 131 | Et | Et | tert-Bu | tert-Bu | Me | Me | H | Me | BArF$_4$ |
| 132 | n-Pr | n-Pr | i-Pr | i-Pr | Me | Me | H | Me | BArF$_4$ |
| 133 | n-Pr | n-Pr | tert-Bu | tert-Bu | Me | Me | H | Me | BArF$_4$ |
| 134 | 1-Ada | 1-Ada | i-Pr | i-Pr | Me | Me | H | Me | BArF$_4$ |
| 135 | 1-Ada | 1-Ada | tert-Bu | tert-Bu | Me | Me | H | Me | BArF$_4$ |
| 136 | i-Pr | i-Pr | i-Pr | i-Pr | Me | Me | H | Me | BF$_4$ |
| 137 | i-Pr | i-Pr | tert-Bu | tert-Bu | Me | Me | H | Me | BF$_4$ |
| 138 | i-Pr | i-Pr | NeoPen | NeoPen | Me | Me | H | Me | BF$_4$ |
| 139 | i-Pr | i-Pr | CyHex | CyHex | Me | Me | H | Me | BF$_4$ |
| 140 | i-Pr | i-Pr | Me | Me | Me | Me | H | Me | BF$_4$ |
| 141 | tert-Bu | tert-Bu | i-Pr | i-Pr | Me | Me | H | Me | BF$_4$ |
| 142 | tert-Bu | tert-Bu | tert-Bu | tert-Bu | Me | Me | H | Me | BF$_4$ |
| 143 | tert-Bu | tert-Bu | NeoPen | NeoPen | Me | Me | H | Me | BF$_4$ |
| 144 | tert-Bu | tert-Bu | CyHex | CyHex | Me | Me | H | Me | BF$_4$ |
| 145 | tert-Bu | tert-Bu | Me | Me | Me | Me | H | Me | BF$_4$ |
| 146 | NeoPen | NeoPen | i-Pr | i-Pr | Me | Me | H | Me | BF$_4$ |
| 147 | NeoPen | NeoPen | tert-Bu | tert-Bu | Me | Me | H | Me | BF$_4$ |
| 148 | NeoPen | NeoPen | NeoPen | NeoPen | Me | Me | H | Me | BF$_4$ |
| 149 | CyHex | CyHex | i-Pr | i-Pr | Me | Me | H | Me | BF$_4$ |
| 150 | Me | Me | i-Pr | i-Pr | Me | Me | H | Me | BF$_4$ |
| 151 | Et | Et | tert-Bu | tert-Bu | Me | Me | H | Me | BF$_4$ |
| 152 | 1-Ada | 1-Ada | i-Pr | i-Pr | Me | Me | H | Me | BF$_4$ |

TABLE I-continued

| Compound No. | R 1a | R 1b | R 2a | R 2b | 6 | 7 | 8 | 9 | X |
|---|---|---|---|---|---|---|---|---|---|
| 153 | i-Pr | i-Pr | tert-Bu | tert-Bu | Me | Me | H | Me | PF$_6$ |
| 154 | i-Pr | i-Pr | NeoPen | NeoPen | Me | Me | H | Me | PF$_6$ |
| 155 | tert-Bu | tert-Bu | i-Pr | i-Pr | Me | Me | H | Me | PF$_6$ |
| 156 | tert-Bu | tert-Bu | NeoPen | NeoPen | Me | Me | H | Me | PF$_6$ |
| 157 | NeoPen | NeoPen | i-Pr | i-Pr | Me | Me | H | Me | PF$_6$ |
| 158 | NeoPen | NeoPen | tert-Bu | tert-Bu | Me | Me | H | Me | PF$_6$ |
| 159 | CyHex | CyHex | i-Pr | i-Pr | Me | Me | H | Me | PF$_6$ |
| 160 | Me | Me | i-Pr | i-Pr | Me | Me | H | Me | PF$_6$ |
| 161 | Et | Et | tert-Bu | tert-Bu | Me | Me | H | Me | PF$_6$ |
| 162 | 1-Ada | 1-Ada | i-Pr | i-Pr | Me | Me | H | Me | PF$_6$ |
| 163 | i-Pr | i-Pr | tert-Bu | tert-Bu | Me | Me | H | Me | ArF |
| 164 | i-Pr | i-Pr | NeoPen | NeoPen | Me | Me | H | Me | ArF |
| 165 | tert-Bu | tert-Bu | i-Pr | i-Pr | Me | Me | H | Me | ArF |
| 166 | tert-Bu | tert-Bu | NeoPen | NeoPen | Me | Me | H | Me | ArF |
| 167 | NeoPen | NeoPen | i-Pr | i-Pr | Me | Me | H | Me | ArF |
| 168 | NeoPen | NeoPen | tert-Bu | tert-Bu | Me | Me | H | Me | ArF |
| 169 | CyHex | CyHex | i-Pr | i-Pr | Me | Me | H | Me | ArF |
| 170 | Me | Me | i-Pr | i-Pr | Me | Me | H | Me | ArF |
| 171 | Et | Et | tert-Bu | tert-Bu | Me | Me | H | Me | ArF |
| 172 | 1-Ada | 1-Ada | i-Pr | i-Pr | Me | Me | H | Me | ArF |

In the case where neither of $R^{11}$ nor $R^{12}$ exists in formula (VI) (i.e. there is no substituent of $R^{11}$ or $R^{12}$ in either of the benzene rings), specific examples of the organometallic compounds represented by the following formula (VIa) are shown in Table II.

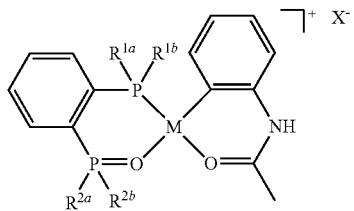

(VIa)

The symbols in Table II have the same meanings as those in Table I.

TABLE II

| Compound No. | R 1a | R 1b | R 2a | R 2b | X |
|---|---|---|---|---|---|
| 201 | i-Pr | i-Pr | i-Pr | i-Pr | SbF$_6$ |
| 202 | i-Pr | tert-Bu | i-Pr | i-Pr | SbF$_6$ |
| 203 | i-Pr | i-Pr | tert-Bu | i-Pr | SbF$_6$ |
| 204 | i-Pr | tert-Bu | i-Pr | tert-Bu | SbF$_6$ |
| 205 | i-Pr | tert-Bu | tert-Bu | tert-Bu | SbF$_6$ |
| 206 | i-Pr | i-Pr | tert-Bu | tert-Bu | SbF$_6$ |
| 207 | i-Pr | i-Pr | NeoPen | NeoPen | SbF$_6$ |
| 208 | i-Pr | tert-Bu | NeoPen | NeoPen | SbF$_6$ |
| 209 | i-Pr | i-Pr | i-Pr | NeoPen | SbF$_6$ |
| 210 | i-Pr | i-Pr | CyHex | CyHex | SbF$_6$ |
| 211 | i-Pr | i-Pr | Me | Me | SbF$_6$ |
| 212 | i-Pr | i-Pr | Et | Et | SbF$_6$ |
| 213 | i-Pr | i-Pr | n-Pr | n-Pr | SbF$_6$ |
| 214 | tert-Bu | tert-Bu | i-Pr | i-Pr | SbF$_6$ |
| 215 | tert-Bu | tert-Bu | tert-Bu | tert-Bu | SbF$_6$ |
| 216 | tert-Bu | tert-Bu | tert-Bu | i-Pro | SbF$_6$ |
| 217 | tert-Bu | tert-Bu | NeoPen | NeoPen | SbF$_6$ |
| 218 | tert-Bu | tert-Bu | CyHex | CyHex | SbF$_6$ |
| 219 | tert-Bu | tert-Bu | CyPen | CyPen | SbF$_6$ |
| 220 | tert-Bu | tert-Bu | Me | Me | SbF$_6$ |
| 221 | tert-Bu | tert-Bu | Et | Et | SbF$_6$ |
| 222 | tert-Bu | tert-Bu | n-Pr | n-Pr | SbF$_6$ |
| 223 | NeoPen | NeoPen | i-Pr | i-Pr | SbF$_6$ |
| 224 | NeoPen | NeoPen | tert-Bu | tert-Bu | SbF$_6$ |
| 225 | NeoPen | NeoPen | NeoPen | NeoPen | SbF$_6$ |
| 226 | NeoPen | NeoPen | CyHex | CyHex | SbF$_6$ |
| 227 | NeoPen | NeoPen | Me | Me | SbF$_6$ |
| 228 | NeoPen | NeoPen | Et | Et | SbF$_6$ |
| 229 | NeoPen | NeoPen | n-Pr | n-Pr | SbF$_6$ |
| 230 | CyHex | CyHex | i-Pr | i-Pr | SbF$_6$ |
| 231 | CyHex | CyHex | tert-Bu | tert-Bu | SbF$_6$ |
| 232 | CyHex | CyHex | NeoPen | NeoPen | SbF$_6$ |
| 233 | CyHex | CyHex | Me | Me | SbF$_6$ |
| 234 | CyPen | CyPen | i-Pr | i-Pr | SbF$_6$ |
| 235 | CyPen | CyPen | tert-Bu | tert-Bu | SbF$_6$ |
| 236 | Me | Me | i-Pr | i-Pr | SbF$_6$ |
| 237 | Me | Me | tert-Bu | tert-Bu | SbF$_6$ |
| 238 | Me | Me | NeoPen | NeoPen | SbF$_6$ |
| 239 | Me | Me | CyHex | CyHex | SbF$_6$ |
| 240 | Et | Et | i-Pr | i-Pr | SbF$_6$ |
| 241 | Et | Et | tert-Bu | tert-Bu | SbF$_6$ |
| 242 | Et | Et | NeoPen | NeoPen | SbF$_6$ |
| 243 | Et | Et | Me | Me | SbF$_6$ |
| 244 | n-Pr | n-Pr | i-Pr | i-Pr | SbF$_6$ |
| 245 | n-Pr | n-Pr | tert-Bu | tert-Bu | SbF$_6$ |
| 246 | n-Pr | n-Pr | NeoPen | NeoPen | SbF$_6$ |
| 247 | n-Pr | n-Pr | CyHex | CyHex | SbF$_6$ |
| 248 | 1-Ada | 1-Ada | i-Pr | i-Pr | SbF$_6$ |
| 249 | 1-Ada | 1-Ada | tert-Bu | tert-Bu | SbF$_6$ |
| 250 | 1-Ada | 1-Ada | NeoPen | NeoPen | SbF$_6$ |
| 251 | 1-Ada | 1-Ada | Me | Me | SbF$_6$ |
| 252 | 1-Ada | 1-Ada | Et | Et | SbF$_6$ |
| 253 | HIPT | HIPT | i-Pr | i-Pr | SbF$_6$ |
| 254 | HIPT | HIPT | tert-Bu | tert-Bu | SbF$_6$ |
| 255 | HIPT | HIPT | NeoPen | NeoPen | SbF$_6$ |
| 256 | HIPT | HIPT | Me | Me | SbF$_6$ |
| 257 | Biph | Biph | i-Pr | i-Pr | SbF$_6$ |
| 258 | Biph | Biph | tert-Bu | tert-Bu | SbF$_6$ |
| 259 | Biph | Biph | NeoPen | NeoPen | SbF$_6$ |
| 260 | Biph | Biph | Me | Me | SbF$_6$ |
| 261 | i-Pr | i-Pr | i-Pr | i-Pr | BArF$_4$ |
| 262 | i-Pr | i-Pr | tert-Bu | tert-Bu | BArF$_4$ |
| 263 | i-Pr | i-Pr | NeoPen | NeoPen | BArF$_4$ |
| 264 | i-Pr | i-Pr | CyHex | CyHex | BArF$_4$ |
| 265 | i-Pr | i-Pr | Me | Me | BArF$_4$ |
| 266 | i-Pr | i-Pr | Et | Et | BArF$_4$ |
| 267 | tert-Bu | tert-Bu | i-Pr | i-Pr | BArF$_4$ |

TABLE II-continued

| Compound No. | R 1a | 1b | 2a | 2b | X |
|---|---|---|---|---|---|
| 268 | tert-Bu | tert-Bu | tert-Bu | tert-Bu | BArF$_4$ |
| 269 | tert-Bu | tert-Bu | NeoPen | NeoPen | BArF$_4$ |
| 270 | tert-Bu | tert-Bu | CyHex | CyHex | BArF$_4$ |
| 271 | tert-Bu | tert-Bu | Me | Me | BArF$_4$ |
| 272 | tert-Bu | tert-Bu | Et | Et | BArF$_4$ |
| 273 | tert-Bu | tert-Bu | n-Pr | n-Pr | BArF$_4$ |
| 274 | NeoPen | NeoPen | i-Pr | i-Pr | BArF$_4$ |
| 275 | NeoPen | NeoPen | tert-Bu | tert-Bu | BArF$_4$ |
| 276 | NeoPen | NeoPen | NeoPen | NeoPen | BArF$_4$ |
| 277 | NeoPen | NeoPen | CyHex | CyHex | BArF$_4$ |
| 278 | NeoPen | NeoPen | Me | Me | BArF$_4$ |
| 279 | CyHex | CyHex | i-Pr | i-Pr | BArF$_4$ |
| 280 | CyHex | CyHex | tert-Bu | tert-Bu | BArF$_4$ |
| 281 | CyPen | CyPen | i-Pr | i-Pr | BArF$_4$ |
| 282 | CyPen | CyPen | tert-Bu | tert-Bu | BArF$_4$ |
| 283 | Me | Me | i-Pr | i-Pr | BArF$_4$ |
| 284 | Me | Me | tert-Bu | tert-Bu | BArF$_4$ |
| 285 | Et | Et | i-Pr | i-Pr | BArF$_4$ |
| 286 | Et | Et | tert-Bu | tert-Bu | BArF$_4$ |
| 287 | n-Pr | n-Pr | i-Pr | i-Pr | BArF$_4$ |
| 288 | n-Pr | n-Pr | tert-Bu | tert-Bu | BArF$_4$ |
| 289 | 1-Ada | 1-Ada | i-Pr | i-Pr | BArF$_4$ |
| 290 | 1-Ada | 1-Ada | tert-Bu | tert-Bu | BArF$_4$ |
| 291 | i-Pr | i-Pr | i-Pr | i-Pr | BF$_4$ |
| 292 | i-Pr | i-Pr | tert-Bu | tert-Bu | BF$_4$ |
| 293 | i-Pr | i-Pr | NeoPen | NeoPen | BF$_4$ |
| 294 | i-Pr | i-Pr | CyHex | CyHex | BF$_4$ |
| 295 | i-Pr | i-Pr | Me | Me | BF$_4$ |
| 296 | tert-Bu | tert-Bu | i-Pr | i-Pr | BF$_4$ |
| 297 | tert-Bu | tert-Bu | tert-Bu | tert-Bu | BF$_4$ |
| 298 | tert-Bu | tert-Bu | NeoPen | NeoPen | BF$_4$ |
| 299 | tert-Bu | tert-Bu | CyHex | CyHex | BF$_4$ |
| 300 | tert-Bu | tert-Bu | Me | Me | BF$_4$ |
| 301 | NeoPen | NeoPen | i-Pr | i-Pr | BF$_4$ |
| 302 | NeoPen | NeoPen | tert-Bu | tert-Bu | BF$_4$ |
| 303 | NeoPen | NeoPen | NeoPen | NeoPen | BF$_4$ |
| 304 | CyHex | CyHex | i-Pr | i-Pr | BF$_4$ |
| 305 | Me | Me | i-Pr | i-Pr | BF$_4$ |
| 306 | Et | Et | tert-Bu | tert-Bu | BF$_4$ |
| 307 | 1-Ada | 1-Ada | i-Pr | i-Pr | BF$_4$ |
| 308 | i-Pr | i-Pr | tert-Bu | tert-Bu | PF$_6$ |
| 309 | i-Pr | i-Pr | NeoPen | NeoPen | PF$_6$ |
| 310 | tert-Bu | tert-Bu | i-Pr | i-Pr | PF$_6$ |
| 311 | tert-Bu | tert-Bu | NeoPen | NeoPen | PF$_6$ |
| 312 | NeoPen | NeoPen | i-Pr | i-Pr | PF$_6$ |
| 313 | NeoPen | NeoPen | tert-Bu | tert-Bu | PF$_6$ |
| 314 | CyHex | CyHex | i-Pr | i-Pr | PF$_6$ |
| 315 | Me | Me | i-Pr | i-Pr | PF$_6$ |
| 316 | Et | Et | tert-Bu | tert-Bu | PF$_6$ |
| 317 | 1-Ada | 1-Ada | i-Pr | i-Pr | PF$_6$ |
| 318 | i-Pr | i-Pr | tert-Bu | tert-Bu | ArF |
| 319 | i-Pr | i-Pr | NeoPen | NeoPen | ArF |
| 320 | tert-Bu | tert-Bu | i-Pr | i-Pr | ArF |
| 321 | tert-Bu | tert-Bu | NeoPen | NeoPen | ArF |
| 322 | NeoPen | NeoPen | i-Pr | i-Pr | ArF |
| 323 | NeoPen | NeoPen | tert-Bu | tert-Bu | ArF |
| 324 | CyHex | CyHex | i-Pr | i-Pr | ArF |
| 325 | Me | Me | i-Pr | i-Pr | ArF |
| 326 | Et | Et | tert-Bu | tert-Bu | ArF |
| 327 | 1-Ada | 1-Ada | i-Pr | i-Pr | ArF |

The organometallic compounds represented by formulae (II) to (VI) of the present invention can be suitably used as a catalyst for polymerizing vinyl monomers. The catalyst composition containing the organometallic compound represented by formulae (II) to (VI) of the present invention can be used for homopolymerization of non-polar olefins, as well as copolymerization of non-polar olefins and polar olefins.

The organometallic compounds represented by formulae (II) to (VI) do not need to be isolated and the reaction solution for preparing the same can be used as it is as a catalyst composition for polymerization.

The catalyst composition of the present invention can be used for homopolymerization of non-polar olefins. Non-polar olefins are selected from, for example, α-olefins such as ethylene, propylene, 1-butene, 2-butene, isobutene, 1-pentene, 1-hexene, 1-heptene, 1-octene, 1,5-hexadiene, 1,7-octadiene, cyclopentadiene, norbornadiene; and combination thereof. Suitable non-polar olefin may be ethylene.

The catalyst composition of the present invention can be used for copolymerization of the above-mentioned non-polar olefins and polar olefins. The polar olefins to be used is at least one member selected from the group consisting of vinyl ester such as vinyl formate, vinyl acetate, vinyl n-propionate, vinyl butyrate, vinyl isobutyrate, vinyl pivalate, vinyl versatate, vinyl 2-ethylhexanoate, vinyl benzoate and isopropenyl acetate; vinyl chloride; vinyl ether such as methyl vinyl ether, ethyl vinyl ether, n-propyl vinyl ether, n-butyl vinyl ether, i-butyl vinyl ether, t-butyl vinyl ether and phenyl vinyl ether; acrylic ester such as methyl acrylate, ethyl acrylate, n-propyl acrylate, n-butyl acrylate, dodecyl acrylate and phenyl acrylate; methacrylic ester such as methyl methacrylate, ethyl methacrylate, n-propyl methacrylate, n-butyl methacrylate, dodecyl methacrylate and phenyl methacrylate; and acrylonitrile.

In the present invention, polar olefin may be an allyl compound containing a polar group. Examples of an allyl compound containing a polar group include allyl acetate, allyl trifluoroacetate, allyl alcohol, allyl methyl ether, allyl ethyl ether, allyl n-propyl ether, allyl n-butyl ether, allyl t-butyl ether, allyl phenyl ether, allyl chloride, allyl bromide, allylamine, allylamine hydrochloride, N-allylaniline, N-t-butoxycarbonyl-N-allylamine and N-benzyloxycarbonyl-N-allylamine.

In the present invention, polar-olefins may be vinyl ketone monomer. Examples of vinyl ketone include 1-pentadecene-3-one, 1-heptene-3-one, 1-decene-3-one, 3-butene-2-one, 1-nonadecene-3-one, 1-octene-3-one, 1-heptene-3-one, 1-hexene-3-one, 1-pentene-3-one and 1-phenyl-2-propene-1-one.

In the present invention, polar olefins may be N-vinyl monomer. N-vinyl monomer may be selected from N-vinylpyrrolidone, N-vinylcaprolactam, N-vinylformamide; N-vinylacetamide; N-vinylphthalimide; N-methylvinylacetamide; N-vinylcaprolactam; 5-ethyl-5-methyl-3-vinyl-hydantoin; 5 methyl-5-phenyl-3-vinyl-hydantoin; N-vinylcarbazole; N,N-dimethylacrylamide; 5-pentamethylene-3-vinyl-hydantoin and the like.

In the present invention, polar olefin may be polar norbornene monomer, vinylphosphonate, and ester thereof.

Preferred polar olefins in the present inventions are vinyl acetate, vinyl benzoate, acrylonitrile, methyl vinyl ether, ethyl vinyl ether, butyl vinyl ether, allyl acetate, allyl trifluoroacetate, allyl alcohol, allyl methyl ether, allyl ethyl ether, allyl n-propyl ether, allyl n-butyl ether, allyl t-butyl ether, allyl phenyl ether, allyl chloride, allyl bromide, allylamine, allylamine hydrochloride, N-allylaniline, N-t-butoxycarbonyl-N-allylamine and N-benzyloxycarbonyl-N-allylamine.

The method for producing copolymer of non-polar olefins and polar olefins of the present invention can be conducted at a temperature of 30° C. or higher and 150° C. or lower. The polymerization pressure may vary depending on the catalyst component activity and selected non-polar olefins and polar olefins. Typically, a gaseous monomer such as ethylene requires high pressure. Polymerization pressure is 0.50 atmosphere or higher and 200 atmosphere and lower.

Furthermore, the molar ratio of the polar olefin monomer to the organometallic complex in the present invention is 20:1 to 500,000:1. With respect to a gaseous monomer under high pressure, especially at a given pressure such as 400 psi or higher, the molar ratio of the non-polar olefin to the organometallic complex in the present invention may be 5,000,000:1 or higher, for example, 6,000,000:1 or lower, 8,000,000:1 or lower or even higher than that. In the polymerization method of the present invention, the amount of the diluent is 0.0 or higher and 10,000 or less when it is expressed as the diluent volume (ml) per millimole of the organometallic complex of the present invention.

The organometallic compound of the present invention can be used for polymerization by allowing it to be supported on a carrier. There is no particular limitation on the carrier in this case, and examples thereof include inorganic carriers such as silica gel and alumina, and organic carriers such as polystyrene, polyethylene and polypropylene. Examples of the method for supporting a metal complex include a physical adsorption method by impregnating the support with a solution of the metal complex and drying it, and a method of supporting the metal complex by chemically bonding the metal complex and the support.

There is no particular limitation on a polymerization method, and the polymerization can be performed by a generally-used method. That is, a process method such as a solution polymerization method, suspension polymerization method and gas phase polymerization method are available. Particularly preferred are a solution polymerization method and a suspension polymerization method. The polymerization style can be either of batch polymerization or continuous polymerization. Also, the polymerization can be conducted either by single-stage polymerization or multistage polymerization.

The polymerization time can be appropriately adjusted depending on the processing mode and the polymerization activity of the catalyst, and can be as short as several minutes or as long as several thousand hours.

It is preferable to fill the atmosphere in the polymerization system with an inert gas such as nitrogen and argon to prevent components other than monomers such as air, oxygen and moisture being mixed into the atmosphere to retain the catalytic activity. In the case of the solution polymerization, an inert solvent may be used in addition to monomers. There are no particular limitations on the inert solvent, and examples include aliphatic hydrocarbon such as pentane, hexane and heptane; alicyclic hydrocarbon such as cyclopentane, cyclohexane and cycloheptane; aromatic hydrocarbon such as benzene, toluene and xylene; halogenated aliphatic hydrocarbon such as chloroform, methylene chloride, carbon tetrachloride, dichloroethane and tetrachloroethane; halogenated aromatic hydrocarbon such as chlorobenzene, dichlorobenzene and trichlorobenzene; aliphatic ester such as methyl acetate and ethyl acetate; and aromatic ester such as methyl benzoate and ethyl benzoate.

After completion of the polymerization reaction, the (co) polymer as a reaction product is to be isolated by post-treatment using a known operation and treating method (e.g. neutralization, extraction with solvents, washing with water, liquid separation, distillation with solvents and reprecipitation).

EXAMPLES

Hereinafter, the present invention is described in greater detail by referring to Examples described below. The present invention is by no means limited thereto. The measuring methods used in Synthesis Examples, Examples and Comparative Examples are as described below.

[Identification of the Organometallic Compound]

$^1$H-NMR, $^{13}$C-NMR and $^{31}$P-NMR spectra were measured using nuclear magnetic resonance apparatus (JNM-ECP500 and JNMECS400 manufactured by JEOL Ltd.). The content of the polar monomer unit in the polymer and the branching degree of the copolymer were determined by analyzing $^{13}$C-NMR spectrum and adding $Cr(acac)_3$ (acac=Acetylacetonate; $CH_3COCHCOCH_3$) as relaxation agent. A molecular weight was calculated by size exclusion chromatography in which polystyrene was employed as an internal standard substance using HLC-8121GPC/HT, manufactured by Tosoh Corporation, provided with TSK gel GMHHR-H(S)HT. The result was adjusted by applying Mark-Houwink parameters for polystyrene ($K=1.75 \times 10^{-2}$ cm$^3$/g, $\alpha=0.67$) and linear low-density polyethylene ($K=5.90 \times 10^{-2}$ cm$^3$/g, $\alpha=0.69$). The elemental analysis was conducted at Microanalytical Laboratory, Department of Chemistry, Graduate School of Science, the University of Tokyo. The high-resolution mass spectrometry (HRMS) was conducted by the electrospray ionization time-of-flight (ESI-TOF) method using TSK gel JMS-T100LP manufactured by JEOL Ltd. in which polyethylene glycol was employed as an internal standard substance.

Synthesis Examples 1 to 4

The following compounds 1 to 4 were synthesized according to the following scheme 1.

Scheme 1

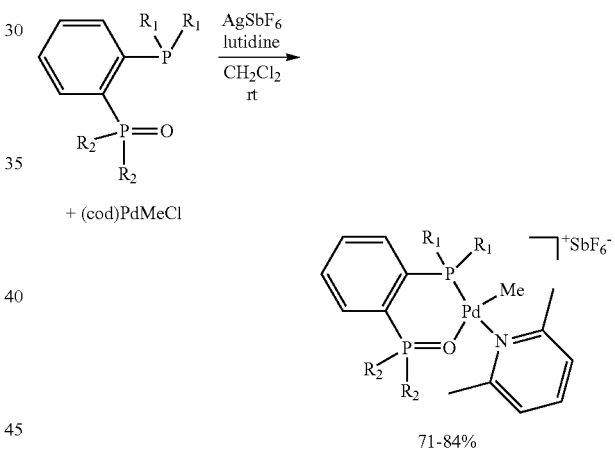

Compound 1: $R^1$=Ph, $R^2$=Ph
Compound 2: $R^1$=Ph, $R^2$=t-Bu
Compound 3: $R^1$=i-Pro, $R^2$=Ph
Compound 4: $R^1$=i-Pro, $R^2$=t-Bu (corresponding to Compound No. 11 in Table I)

Synthesis Example 1

Synthesis of Compound 1 ([methylpalladium(1-diphenylphosphino-2-diphenylphosphinylbenzene) (2,6-lutidine)][hexafluoroantimonate])

As free BPMO (bisphosphine monoxide), after mixing a methylene chloride (2 ml) solution of o-(Ph$_2$P)C$_6$H$_4$(P(O) Ph$_2$)(1-diphenylphosphino-2-dihenylphosphinylbenzene) (139 mg, 0.301 mmol) and a methylene chloride (2 ml) solution of (cod)PdMeCl (cod=1,5-cyclooctadiene; 80 mg, 0.30 mmol) for five minutes at 25° C., toluene and hexane were added to the mixture to thereby obtain 175 mg of ((o-(Ph$_2$P) C$_6$H$_4$(P(O)Ph$_2$)PdMeCl complex as an intermediate. The solid and 2,6-lutidine (0.033 ml, 0.28 mmol) were dissolved in 5 ml of methylene chloride and reacted with silver hexafluoroantimonate (97 mg, 0.28 mmol) at 25° C. for ten minutes. After removing silver chloride by Celite filtration, solvent was distilled away. The resultant was dissolved in trifluoromethyl benzene and ether was added thereto. The precipitate formed was collected and dried, and recrystallized from methylene chloride to thereby obtain 175 mg of Compound 1 in the paragraph title as a pale orange crystals which were stable in air and in humid condition. The yield was 49%.

$^1$H NMR (CD$_2$Cl$_2$, 500 MHz) δ 7.76-7.70 (m, 2H), 7.61-7.29 (m, 20H), 7.24-7.19 (m, 5H), 3.16 (s, 6H), 0.15 (d, J=3.7 Hz, 3H); $^{13}$C-NMR (CD$_2$Cl$_2$, 102 MHz) δ 139.59, 136.73 (dd, J=64, 10 Hz), 134.51 (d, J=12 Hz), 134.05-133.76 (m), 132.60 (d, J=11 Hz), 132.01, 131.45 (d, J=12 Hz), 129.64-129.41 (m), 128.70, 128.46, 128.17, 123.66 (d, J=9 Hz), 26.94, −0.84; $^{31}$P NMR (CD$_2$Cl$_2$, 202 MHz) δ 40.42 (d, J=17 Hz), 29.52 (d, J=17 Hz); $^{19}$F NMR (CD$_2$Cl$_2$, 470 MHz) δ −113.93-134.61 (m); HRMS-ESI (m/z): [M]$^+$ Calc'd for C$_{38}$H$_{36}$NOP$_2$Pd: 690.1307. Found: 690.1313.

Synthesis Example 2

Synthesis of Compound 2 ([methylpalladium(1-diphenylphosphino-2-di(t-butyl)phosphinylbenzene) (2,6-lutidine)][hexafluoroantimonate])

Compound 2 was obtained in the same way as in the case of Compound 1 except that o-(Ph$_2$P)C$_6$H$_4$(P(O)t-Bu$_2$) was used as free BPMO. The yield was 57%.

$^1$H NMR (CD$_2$Cl$_2$, 500 MHz) δ 7.82-7.78 (m, 1H), 7.74 (t, J=7.8 Hz, 2H), 7.64 (t, J=7.8 Hz, 1H), 7.58-7.50 (m, 10H), 7.44 (m, 1H), 7.28 (d, J=7.8 Hz, 2H), 3.14 (s, 6H), 1.08 (d, J=14.4 Hz, 18H), 0.16 (d, J=3.0 Hz, 3H); $^{13}$C-NMR (CD$_2$Cl$_2$, 102 MHz) δ 158.95, 139.59, 138.38 (dd, J=8.3 Hz), 134.54 (d, J=12 Hz), 134.21-133.28 (m), 132.59 (dd, J=7.3 Hz), 132.01 (d, J=2 Hz), 130.88 (dd, J=12.2 Hz), 130.01, 129.61 (d, J=11 Hz), 129.50, 123.63 (d, J=4 Hz), 37.95 (d, J=58 Hz), 27.26, 27.00, −2.25; $^{31}$P NMR (CD$_2$Cl$_2$, 202 MHz) δ 62.36, 35.49; Anal. Calc'd for C$_{34}$H$_{44}$F$_6$NOP$_2$PdSb: C, 46.05; H, 5.00; N, 1.58. Found: C, 45.86; H, 5.28; N, 1.37.

Synthesis Example 3

Synthesis of Compound 3 ([methylpalladium(1-diisopropylphosphino-2-diphenylphosphinylbenzene) (2,6-lutidine)][hexafluoroantimonate])

Compound 3 was obtained in the same way as in the case of Compound 1 except that o-(i-Pr$_2$P)C$_6$H$_4$(P(O)Ph$_2$) was used as free BPMO. The yield was 49%.

$^1$H NMR (CD$_2$Cl$_2$, 500 MHz) δ 8.05 (dt, J=7.4, 4.4 Hz, 1H), 7.79 (dt, J=7.6, 0.9 Hz, 1H), 7.72-7.65 (m, 3H), 7.57-7.49 (m, 5H), 7.34-7.29 (m, 4H), 7.25 (dddd, J=15.1, 7.9, 3.4, 1.1 Hz, 1H), 7.14 (d, J=7.8 Hz 2H), 2.66 (s, 6H), 1.41 (dd, J=15.1, 6.9 Hz, 6H), 1.27 (d, J=17.6, 7.1 Hz, 6H), 0.33 (d, J=2.3 Hz, 3H); $^{13}$C-NMR (CD$_2$Cl$_2$, 102 MHz) δ 158.99, 139.38, 136.48 (dd, J=15.9 Hz), 134.58 (d, J=10 Hz), 134.73 (dd, J=100, 12.5 Hz), 134.25 (d, J=3 Hz), 133.21 (dd, J=6.3 Hz), 132.91 (d, J=11 Hz), 131.27 (d, J=6 Hz), 131.11, 130.23, 129.73 (d, J=13 Hz), 123.45 (d, J=3 Hz), 27.17 (d, J=26 Hz), 26.27, 19.62 (d, J=4 Hz), 18.86, −6.33 (d, J=4 Hz); $^{31}$P NMR (CD$_2$Cl$_2$, 202 MHz) δ 42.74 (d, J=9 Hz), 42.23 (d, J=9 Hz); Anal. Calc'd for C$_{32}$H$_{40}$F$_6$NOP$_2$PdSb: C, 44.75; H, 4.69; N, 1.63. Found: C, 44.55; H, 4.69; N, 1.52.

Synthesis Example 4

Synthesis of Compound 4 ([methylpalladium(1-diisopropylphosphino-2-di(t-butyl)phosphinylbenzene) (2,6-lutidine)][hexafluoroantimonate])

Compound 4 was obtained in the same way as in the case of Compound 1 except that o-(i-Pr$_2$P)C$_6$H$_4$(P(O)t-Bu$_2$) was used as free BPMO. The yield was 72%.

$^1$H NMR (CD$_2$Cl$_2$, 500 MHz) δ 8.04 (dt, J=7.7 Hz, 3.9 Hz, 1H), 7.80-7.71 (m, 4H), 7.26 (d, J=7.8 Hz, 2H), 3.14 (s, 6H), 2.73-2.65 (m, 2H), 1.35-1.29 (m, 12H), 1.22 (d, J=14.4 Hz, 18H), 0.39 (d, J=2.1 Hz, 3H); $^{13}$C-NMR (CDCl$_3$, 102 MHz) δ 158.75, 139.38, 135.20 (d, J=9 Hz), 134.47 (d, J=12 Hz), 133.32-133.11 (m), 132.29 (dd, J=6, 3 Hz), 130.52 (d, J=12 Hz), 123.62 (d, J=3 Hz), 38.27 (d, J=57 Hz), 29.01 (d, J=26 Hz), 27.80, 26.91, 20.13 (d, J=4 Hz), 19.47, −8.11; $^{31}$P NMR (CD$_2$Cl$_2$, 202 MHz) δ 58.22, 44.85; Anal. Calc'd for C$_{28}$H$_{48}$F$_6$NOP$_2$PdSb: C, 41.07; H, 5.91; N, 1.71. Found: C, 40.90; H, 5.96; N, 1.65.

Synthesis Examples 5 to 6

Next, Compounds 5 to 6 were synthesized according to the following scheme 2.

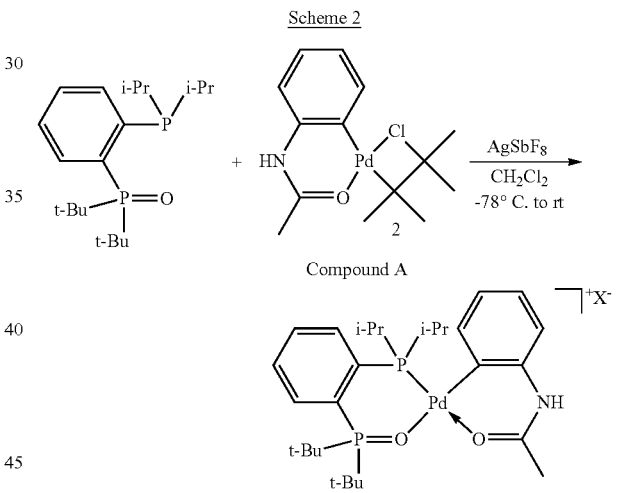

Scheme 2

Compound 5: X=SbF$_6$ (corresponding to Compound No. 206 in Table II)
Compound 6: X=BArF$_4$ (corresponding to Compound No. 262 in Table II)

Compound A (acetanilide palladium chloride dimer) was synthesized according to the method described in a literature (Chem. Eur. J. 2010, 16, 4010-4017).

Synthesis Example 5

Synthesis of Compound 5 ([κ2-(o-acetanilide)palladium(1-diisopropylphosphino-2-di(t-butyl)phosphinylbenzene) (2,6-lutidine)][hexafluoroantimonate]

o-(i-Pr$_2$P)C$_6$H$_4$ (P(O)t-Bu$_2$) (142 mg, 0.401 mmol) as free BPMO and Compound A (110 mg, 0.199 mmol) were dissolved in 7 ml of methylene chloride and stirred at 25° C. for three hours. The solution was poured slowly into silver hexafluoroantimonate (0.31 g, 0.90 mmol) in a flask cooled to −78° C. After vigorous stirring at 25° C. for 30 minutes, the resultant solution was condensed by removing silver chloride through Celite filtration. Toluene was poured into the solution to obtain precipitate. The precipitate was recrystallized from methylene chloride to thereby obtain Compound 5 as a pale orange crystals which were stable in air and humid condition. The yield was 73%.

$^1$H NMR (CD$_2$Cl$_2$, 500 MHz) δ 8.96 (s, 1H), 8.00-7.97 (m, 1H), 7.81-7.72 (m, 3H), 7.24 (ddd, J=7.7, 4.7, 1.1 Hz, 1H), 7.09 (t, J=7.1 Hz, 1H), 6.98-6.92 (m, 2H), 2.41 (s, 3H), 1.42 (d, J=14.4 Hz, 18H), 1.22 (dd, J=15.4, 7.1 Hz, 6H), 1.03 (dd, J=18.3, 7.1 Hz, 6H); $^{13}$C-NMR (CD$_2$Cl$_2$, 102 MHz) δ 172.55 (d, J=3 Hz), 138.26 (d, J=7 Hz), 135.80 (d, J=9 Hz), 135.12, 134.36 (d, J=11 Hz), 133.35 (dd, J=13.8 Hz), 132.17 (dd, J=6.3 Hz), 131.46 (dd, J=33.4 Hz), 130.73 (dd, J=−12.2 Hz), 126.49, 125.51 (d, J=4 Hz), 125.19 (d, J=2 Hz), 118.50, 38.04 (d, J=57 Hz), 27.83, 27.76 (d, J=24 Hz), 22.49 (d, J=4 Hz), 19.99 (d, J=4 Hz), 19.28; $^{31}$P NMR (CD$_2$Cl$_2$, 202 MHz) δ 63.07, 52.30; Anal. Calc'd for C$_{28}$H$_{44}$F$_6$NOP$_2$PdSb: C, 40.48; H, 5.34; N, 1.69. Found: C, 40.20; H, 5.41; N, 1.53.

Example 6

Synthesis of Compound 6 ([2-(o-acetanilide)palladium(1-diisopropylphosphino-2-di(t-butyl)phosphinylbenzene)(2,6-lutidine)][tetrakis(3,5-bis(trifluoromethyl)phenylborate]

Compound 6 was obtained in the same way as in the case of Compound 5 except that NaBArF$_4$ was used instead of silver hexafluoroantimonate. The yield was 96%.

$^1$H NMR (CD$_2$Cl$_2$, 500 MHz) δ 8.27 (s, 1H), 7.98-7.94 (m, 1H), 7.87-7.69 (m, 11H), 7.56 (s, 4H), 7.26 (ddd, J=7.8, 4.6, 1.1 Hz, 1H), 7.12 (t, J=7.8 Hz, 1H), 7.00 (t, J=7.8 Hz, 1H), 6.82 (dd, J=7.8, 1.4 Hz, 1H), 2.80-2.73 (m, 2H), 2.40 (s, 3H), 1.41 (d, J=14.4 Hz, 18H), 1.21 (dd, J=15.4, 6.9 Hz, 6H), 1.01 (dd, J=18.3, 7.1 Hz, 6H); $^{13}$C-NMR (CDCl$_3$, 102 MHz) δ 172.34 (d, J=3 Hz), 162.40 (q, J=50 Hz), 138.59 (d, J=7 Hz), 135.74 (d, J=10 Hz), 135.42, 135.18 (d, J=12 Hz), 134.82, 134.45 (d, J=11 Hz), 133.42 (dd, J=13.8 Hz), 132.21 (dd, J=6.3 Hz), 131.27 (dd, J=34.4 Hz), 130.83 (dd, J=−12.2 Hz), 129.51 (qq, J=32.3 Hz), 126.66, 126.02 (d, J=4 Hz), 125.30 (d, J=2 Hz), 125.21 (q, J=272 Hz), 118.15, 38.12 (d, J=58 Hz), 27.80, 27.75 (d, J=25 Hz), 22.88 (d, J=3 Hz), 19.93 (d, J=4 Hz), 19.24; $^{31}$P NMR (CD$_2$Cl$_2$, 202 MHz) δ 63.03, 52.65; $^{19}$F NMR (CD$_2$Cl$_2$, 470 MHz) δ −62.73; Anal. Calc'd for C$_{60}$H$_{56}$BF$_{24}$NO$_2$P$_2$Pd: C, 49.42; H, 3.87; N, 0.96. Found: C, 49.18; H, 4.09; N, 0.84.

Synthesis Example 7

Synthesis of Compound 7 ([methylpalladium(1-diisopropylphosphino-2-di(t-butyl)phosphinylbenzene)(2,6-lutidine)][tetrakis(3,5-bis(trifluoromethyl)phenyl)borate]

Compound 7 was synthesized using Compound 4 as a raw material. That is, a methylene chloride suspension (8 ml) of ([methylpalladium(1-diisopropylphosphino-2-di(t-butyl)phosphinylbenzene)(2,6-lutidine)][hexafluoroantimonate) (Compound 4; 0.24 g; 0.30 mmol) and sodium[tetrakis(3,5-bis(trifluoromethyl)phenyl]borate (0.26 g, 0.30 mmol) was stirred at room temperature for 20 minutes under argon atmosphere. The reaction solution was filtered through a pad of Celite (dried diatom) and the filtrate was subjected to vacuum concentration. The yellow solid residue was washed with hexane, and dried under reduced pressure to obtain 0.14 g of Compound 7. The yield was 95%.

$^1$H NMR (CDCl$_3$) δ 7.97 (td, J=7.6, 3.7 Hz, 1H), 7.71 (s, 8H), 7.68-7.59 (m, 4H), 7.51 (s, 4H), 7.17 (d, J=7.5 Hz, 2H), 3.09 (s, 6H), 2.66-2.57 (m, 2H), 1.30-1.25 (m, 12H), 1.16 (d, J=14.5 Hz, 18H), 0.37 (d, J=2.0 Hz, 3H); $^{31}$P NMR (202 MHz, CDCl$_3$) δ 58.20, 44.83.

Synthesis Example 8

Synthesis of Compound 7 ([methylpalladium(1-diisopropylphosphino-2-di(t-butyl)phosphinylbenzene)(2,6-lutidine)][tetrakis(3,5-bis(trifluoromethyl)phenyl)borate]

Compound 7 was synthesized using Compound 8 represented by the following formula, which is an intermediate in the synthesis of Compound 4 in Synthesis Example 4, as a material.

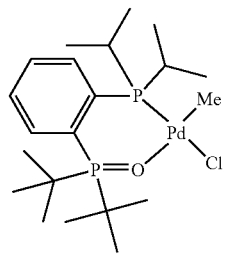

8

That is, a methylene chloride suspension (8 ml) of chloromethylpalladium[1-diisopropylphosphino-2-di(t-butyl)phosphinylbenzene] (Compound 8; 0.10 g; 0.20 mmol), sodium tetrakis[3,5-bis(trifluoromethyl)phenyl]borate (0.18 g, 0.20 mmol) and 2,6-dimethylpyridine (0.021 g, 0.20 mmol) was stirred at room temperature for 20 minutes under argon atmosphere. The reaction mixture was filtered through a pad of Celite (dried diatom) and the filtrate was subjected to vacuum concentration. The yellow solid residue was washed with hexane, and dried under reduced pressure to obtain 0.26 g of Compound 7. The yield was 90%. The $^1$H- and $^{31}$P-NMR spectra of Compound 7 were coincident with those described in Synthesis Example 7.

Synthesis Examples 9 to 12

Compounds 9 to 12 were synthesized according to the following reaction scheme.

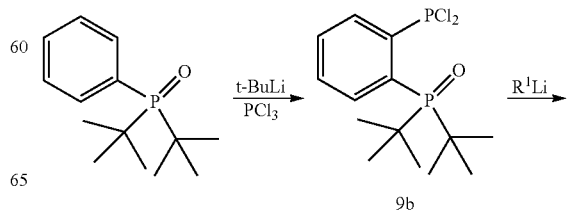

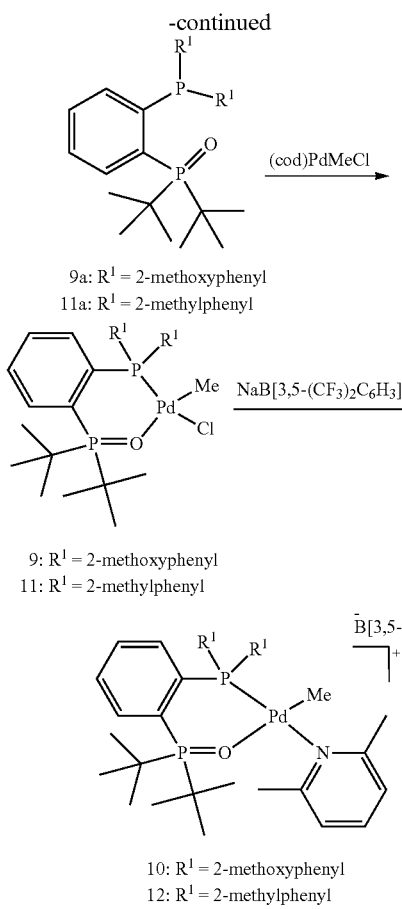

9a: R¹ = 2-methoxyphenyl
11a: R¹ = 2-methylphenyl

9: R¹ = 2-methoxyphenyl
11: R¹ = 2-methylphenyl

10: R¹ = 2-methoxyphenyl
12: R¹ = 2-methylphenyl

Synthesis Example 9

Synthesis of Compound 9 (chloromethylpalladium [1-bis(o-methoxyphenyl)phosphino-2-di(t-butyl) phosphinylbenzene])

The reaction solution between the THF solution (14 ml) of 2-bromoanisole (0.34 g, 2.0 mmol) and n-butyllithium (2.1 mmol in 1.64 M pentane solution; 1.3 ml) was added to the THF solution (7 ml) of Compound 9b (0.37 g, 1.0 mmol) synthesized from lithiated di(t-butyl)phenylphosphineoxide and phosphorus trichloride at −78° C. and stirred for 30 minutes under argon atmosphere. After slowly raising the solution temperature to room temperature, the solution was stirred at room temperature for one hour. The reaction was terminated with water, and after subjecting the reaction solution to vacuum concentration, the residue was dissolved in methylene chloride and the resultant solution was filtered through a pad of Celite. After distilling away the solvent, a purification operation was performed through silica gel-column chromatography using methylene chloride/methanol (30:1) as an eluent and recrystallization from THF/hexane to thereby obtain 0.30 g of Compound 9a.

Furthermore, a methylene chloride solution (3 ml) of the obtained Compound 9a (0.14 g, 0.30 mmol) and (cod)PdMeCl (0.088 g, 0.33 mmol) was stirred at room temperature for one hour under argon atmosphere. The reaction solution was filtered through a pad of Celite (dried diatomite) and the filtrate was subjected to vacuum concentration. The residue was subjected to recrystallization from methylene chloride and diethyl ether to obtain 0.15 g of Compound 9. The yield was 81%.

$^1$H NMR (CD$_2$Cl$_2$) δ 8.68 (br s, 1H), 7.65-7.61 (m, 1H), 7.55-7.53 (m, 1H), 7.50-7.48 (m, 3H), 7.40 (dd, J$_1$=J$_2$=7.7 Hz, 1H), 7.14 (dd, J=J$_2$=7.4 Hz, 1H), 6.99 (dd, J=8.2, 5.5 Hz, 1H), 6.89 (dd, J$_1$=J$_2$=7.3 Hz, 1H), 6.80 (dd, J=8.2, 3.4 Hz, 1H), 6.73 (dd, J=11.6, 7.4 Hz, 1H), 3.69 (s, 3H), 3.41 (s, 3H), 1.45 (d, J=14.2 Hz, 9H), 1.09 (d, J=14.2 Hz, 9H), 0.13 (d, J=3.0 Hz, 3H); $^{31}$P NMR (202 MHz, CD$_2$Cl$_2$) δ 63.46 (s, P(O)t-Bu$_2$), 27.69 (br s, PAr$_2$).

Synthesis Example 10

Synthesis of Compound 10 ([methylpalladium(1-bis (2-methoxyphenyl)phosphino-2-di(t-butyl)phosphinylbenzene)(2,6-lutidine)][tetrakis(3,5-bis(trifluoromethyl)phenylborate])

The methylene chloride suspension (2 ml) of Compound 9 (0.050 g, 0.078 mmol), 2,6-dimethylpyridine (0.013 g, 0.12 mmol) and sodium tetrakis[3,5-bis(trifluoromethyl)phenyl]borate (0.069 g, 0.078 mmol) was stirred under argon atmosphere at room temperature for one hour. The reaction solution was filtered through a pad of Celite (dried diatomite) and the filtrate was subjected to vacuum concentration. The residue was subjected to reprecipitation from methylene chloride and pentane to obtain 0.10 g of Compound 10. The yield was 83%.

$^1$H NMR (CD$_2$Cl$_2$) δ 8.30 (dd, J=15.4, 7.8 Hz, 1H), 7.72 (s, 8H), 7.64-7.57 (m, 10H), 7.49 (dd, J=J$_2$=7.7 Hz, 1H), 7.23 (d, J=8.0 Hz, 1H), 7.19 (d, J=7.5 Hz, 1H), 7.14 (dd, J$_1$=J$_2$=7.4 Hz, 1H), 7.06 (dd, J=8.1, 5.6 Hz, 1H), 6.93-6.90 (m, 2H), 6.68 (dd, J=11.7, 7.8 Hz, 1H), 3.76 (s, 3H), 3.49 (s, 3H), 3.18 (s, 3H), 3.04 (s, 3H), 1.05 (d, J=14.2 Hz, 9H), 1.01 (d, J=14.4 Hz, 9H), −0.01 (d, J=3.0 Hz, 3H); $^{31}$P NMR (202 MHz, CD$_2$Cl$_2$) δ 63.07 (s, P(O)t-Bu$_2$), 25.90 (s, PAr'$_2$); Anal. Calc'd for C$_{68}$H$_{60}$BF$_{24}$NO$_3$P$_2$Pd: C, 51.88; H, 3.84; N, 0.89. Found: C, 51.69; H, 3.89; N, 0.71.

Synthesis Example 11

Synthesis of Compound 11 (chloromethylpalladium [1-bis(2-methylphenyl)phosphino-2-di(t-butyl)phosphinylbenzene])

Compound 11 was synthesized in a similar manner to that described in Synthesis Example 9. That is, a methylene chloride solution (2 ml) of Compound 11a (0.10 g, 0.22 mmol) synthesized from Compound 9a and (cod)PdMeCl (0.064 g, 0.24 mmol) was stirred at room temperature for one hour under argon atmosphere. The reaction solution was filtered through a pad of Celite (dried diatomite) and the filtrate was subjected to vacuum concentration. The residue was subjected to reprecipitation from methylene chloride and diethyl ether to obtain 0.10 g of Compound 11. The yield was 74%.

$^1$H NMR (CDCl$_3$) δ 7.82-7.78 (m, 1H), 7.63 (dd, J$_1$=J$_2$=7.6 Hz, 1H), 7.51 (dd, J$_1$=J$_2$=7.4 Hz, 1H), 7.42-7.35 (m, 4H), 7.26 (dd, J$_1$=J$_2$=7.9 Hz, 1H), 7.19 (dd, J$_1$=J$_2$=7.2 Hz, 1H), 7.01 (dd, J$_1$=J$_2$=7.6 Hz, 1H), 6.66 (dd, J$_1$=J$_2$=9.4 Hz, 1H), 3.14 (s, 3H), 2.29 (s, 3H), 1.62 (d, J=14.2 Hz, 9H), 1.07 (d, J=14.0 Hz, 9H), 0.54 (d, J=2.7 Hz, 3H); $^{31}$P NMR (202 MHz, CD$_2$Cl$_2$) δ 63.07 (s, P(O)t-Bu$_2$), 25.90 (s, PAr$_2$).

Synthesis Example 12

Synthesis of Compound 12 ([methylpalladium(1-bis (2-methylphenyl)phosphino-2-di(t-butyl)phosphinylbenzene)(2,6-lutidine)][tetrakis(3,5-bis(trifluoromethyl)phenylborate])

Compound 12 was synthesized in a similar manner to that described in Synthesis Example 7. That is, a methylene chloride suspension (3 ml) of Compound 11 (0.082 g, 0.14 mmol), 2,6-dimethylpyridine (0.029 g, 0.27 mmol) and sodium tetrakis[(3,5-bis(trifluoromethyl)phenyl]borate (0.12 g, 0.14 mmol) was stirred at room temperature for 1.5 hour under argon atmosphere. The reaction mixture was filtered through a pad of Celite (dried diatom) and the filtrate was subjected to vacuum concentration. The residue was subjected to reprecipitation from methylene chloride and pentane to obtain 0.19 g of Compound 12. The yield was 90%.

$^1$H NMR (CD$_2$Cl$_2$) δ 7.79-7.46 (m, 21H), 7.32-7.30 (m, 2H), 7.22 (2H, t, J=7.2 Hz), 7.14-7.12 (m, 1H), 6.63 (dd, J=11.3, 8.1 Hz, 1H), 3.12 (s, 3H), 3.09 (s, 3H), 2.94 (s, 3H), 2.28 (s, 3H), 1.04 (d, J=14.4 Hz, 9H), 0.97 (d, J=14.7 Hz, 9H), 0.18 (d, J=2.7 Hz, 3H); $^{31}$P NMR (202 MHz, CD$_2$Cl$_2$) δ 64.25 (s, P(O)t-Bu$_2$), 27.37 (s, PAr'$_2$); Anal. Calc'd for C$_{68}$H$_{60}$BF$_{24}$NOP$_2$Pd: C, 52.95; H, 3.92; N, 0.91.

Found: C, 52.57; H, 3.94; N, 0.57.

Synthesis Examples 13 and 14

Compounds 13 and 14 were synthesized according to the following reaction scheme.

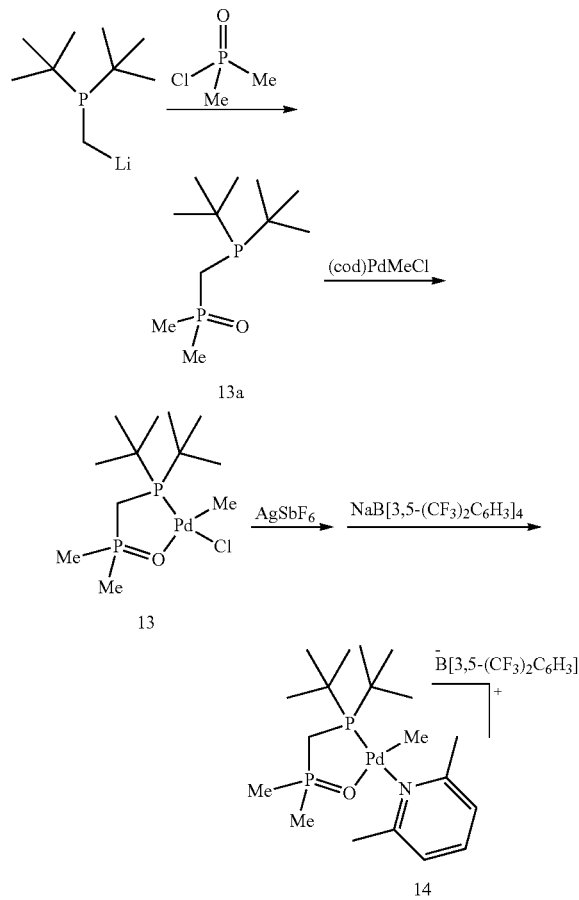

Synthesis Example 13

Synthesis of Compound 13 (chloromethylpalladium [1-di(t-butyl)phosphino-2-dimethylphosphinyl-methane])

A methylene chloride solution (10 ml) of Compound 13a, which is quantitatively obtained from the reaction of di(t-butyl)phosphinomethyllithium (0.083 g, 0.50 mmol) and dimethylphosphinic chloride (0.083 g, 0.50 mmol), and (cod)PdMeCl (0.13 g, 0.50 mmol) was stirred at room temperature under argon atmosphere. The reaction solution was filtered through a pad of Celite (dried diatomite) and the filtrate was subjected to vacuum concentration. The residue was subjected to purification through recrystallization from methylene chloride and hexane to obtain 0.071 g of Compound 13. The yield was 36%.

$^1$H NMR (CD$_2$Cl$_2$) δ 2.32 (dd, J$_1$=J$_2$=9.7 Hz, 2H), 1.78 (d, J=13.1 Hz, 6H), 1.40 (d, J=14.7 Hz, 18H), 0.88 (d, J=2.3 Hz, 3H); $^{31}$P NMR (202 MHz, CD$_2$Cl$_2$) δ 52.40 (d, J=13.1 Hz), 50.83 (d, J=13.1 Hz).

Synthesis Example 14

Synthesis of Compound 14 ([methylpalladium(1-di (t-butyl)phosphino-2-dimethylphosphinylmethane) (2,6-lutidine)][tetrakis(3,5-bis(trifluoromethyl)phenyl)borate])

The methylene chloride suspension (3 ml) of Compound 13 (0.071 g, 0.18 mmol), 2,6-dimethylpyridine (0.019 g, 0.18 mmol) and silver hexafluoroantimonate (0.062 g, 0.18 mmol) was stirred at room temperature under argon atmosphere. After the reaction mixture was filtered through a pad of Celite (dried diatomite), sodium tetrakis(3,5-bis(trifluoromethyl) phenylborate (0.15 g, 0.18 mmol) was added to the filtrate and stirred again at room temperature under argon atmosphere. After the reaction mixture was filtered through a pad of Celite (dried diatomite), the solvent of the filtrate was distilled away to obtain 0.23 g of Compound 14. The yield was 96%.

$^1$H NMR (CD$_2$Cl$_2$) δ 7.74 (s, 8H), 7.66 (t, J=7.7 Hz, 1H), 7.57 (s, 4H), 7.19 (d, J=7.8 Hz, 2H), 2.97 (s, 6H), 2.35 (dd, J$_1$=J$_2$=9.7 Hz, 2H), 1.70 (d, J=12.8 Hz, 6H), 1.45 (d, J=14.9 Hz, 18H), 0.63 (d, J=2.1 Hz, 3H); $^{31}$P NMR (C$_6$D$_6$) δ 58.01 (d, J=8.7 Hz), 53.25 (d, J=8.7 Hz).

Synthesis Examples 15 and 16

Compounds 15 and 16 were synthesized according to the following reaction scheme.

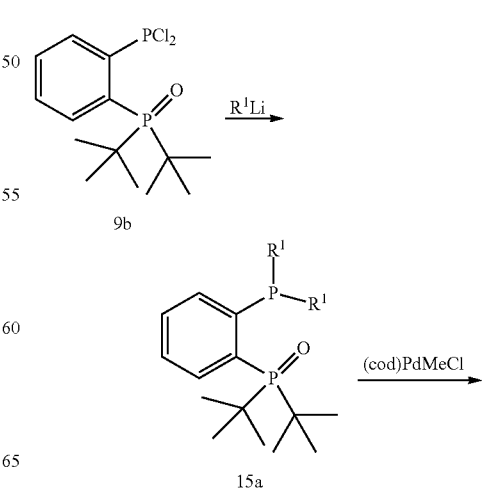

-continued

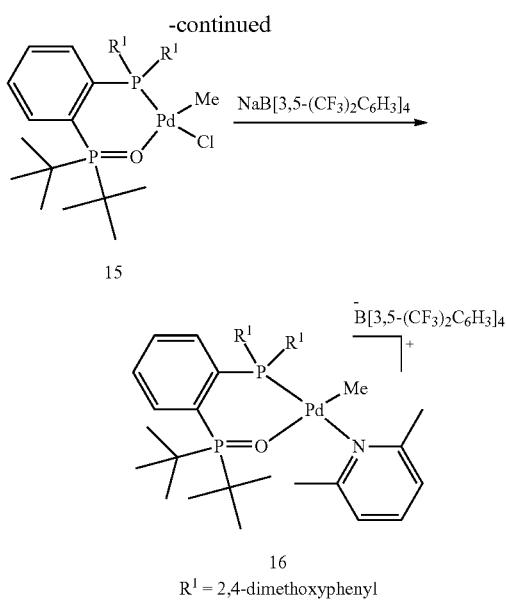

15

16
R¹ = 2,4-dimethoxyphenyl

Synthesis Example 15

Synthesis of Compound 15 (chloromethylpalladium [1-bis(2,4-dimethoxyphenyl)phosphino-2-di(t-butyl) phosphinylbenzene])

Compound 15 was synthesized in a similar manner to that in Synthesis Examples 9 and 11. That is, the reaction solution between the THF solution (14 ml) of 1-bromo-2,4-dimethoxybenzene (0.43 g, 2.0 mmol) and n-butyllithium (2.1 mmol in 1.64 M pentane solution; 1.3 ml) was added to the THF solution (7 ml) of Compound 9b (0.37 g, 1.0 mmol) synthesized from lithiated di(t-butyl)phenylphosphineoxide and phosphorus trichloride at −78° C. and stirred for 30 minutes under argon atmosphere. After slowly raising the solution temperature to room temperature, the solution was stirred at room temperature for one hour. The reaction was terminated with water, and after subjecting the reaction solution to vacuum concentration, the residue was dissolved in methylene chloride and the resultant solution was filtered through a pad of Celite. After distilling away the solvent, a purification operation was performed through recrystallization from methylene chloride/hexane to thereby obtain 0.40 g of Compound 15a.

Furthermore, a methylene chloride solution (2 ml) of the obtained Compound 15a (0.10 g, 0.18 mmol) and (cod)Pd-MeCl (0.054 g, 0.20 mmol) was stirred at room temperature for two hours under argon atmosphere. The reaction solution was filtered through a pad of Celite (dried diatomite) and the filtrate was subjected to vacuum concentration. The residue was subjected to purification by recrystallization from methylene chloride/diethyl ether to obtain 0.098 g of Compound 15. The yield from Compound 9b was 55%.

$^1$H NMR (CD$_2$Cl$_2$) δ 8.75 (br s, 1H), 7.62-7.54 (m, 2H), 7.47-7.45 (m, 1H), 7.38 (t, J=7.7 Hz, 1H), 6.68-6.63 (m, 2H), 6.49 (dd, J=4.1, 2.1 Hz, 1H), 6.42 (d, J=8.5 Hz, 1H), 6.31 (t, J=2.3 Hz, 1H), 3.81 (d, J=2.7 Hz, 6H), 3.65-3.63 (3H, m), 3.35 (3H, s), 1.46 (9H, d, J=14.2 Hz), 1.05 (9H, d, J=14.0 Hz), 0.16 (0.5H, d, J=3.2 Hz), 0.11 (2.5H, d, J=3.0 Hz); $^{31}$P NMR (202 MHz, CD$_2$Cl$_2$) δ 64.19 (s), 27.17 (br s).

Synthesis Example 16

Synthesis of Compound 16 ([methylpalladium(1-bis (2,4-dimethoxyphenyl)phosphino-2-di(t-butyl)phosphinylbenzene)(2,6-lutidine)][tetrakis(3,5-bis(trifluoromethyl)phenylborate])

Compound 16 was synthesized in a similar manner to that in Synthesis Examples 10 and 12. That is, the methylene chloride suspension (4 ml) of Compound 15 (0.098 g, 0.14 mmol), 2,6-dimethylpyridine (0.023 g, 0.27 mmol) and sodium tetrakis(3,5-bis(trifluoromethyl)phenyl]borate (0.12 g, 0.14 mmol) was stirred at room temperature for 40 minutes under argon atmosphere. The residue was subjected to reprecipitation from methylene chloride and pentane to obtain 0.15 g of Compound 16. The yield was 66%.

$^1$H NMR (CD$_2$Cl$_2$) δ 8.34 (1H, dd, J=15.4, 8.7 Hz), 7.72 (t, J=2.2 Hz, 8H), 7.65-7.52 (m, 8H), 7.47 (dd, J$_1$=J$_2$=7.7 Hz, 1H), 7.20 (d, J=7.6 Hz, 1H), 7.17 (d, J=7.6 Hz, 1H), 6.66 (d, J=8.5 Hz, 1H), 6.62 (dd, J=11.7, 8.5 Hz, 1H), 6.58 (dd, J=4.6, 2.3 Hz, 1H), 6.46 (d, J=8.5 Hz, 1H), 6.40 (dd, J$_1$=J$_2$=2.6 Hz, 1H), 3.84 (s, 3H), 3.82 (s, 3H), 3.71 (s, 3H), 3.44 (s, 3H), 3.17 (s, 3H), 3.04 (s, 3H), 1.05 (d, J=14.2 Hz, 9H), 1.00 (d, J=14.4 Hz, 9H), −0.02 (d, J=3.0 Hz, 3H); $^{31}$P NMR (202 MHz, CD$_2$Cl$_2$) δ 62.79 (s), 24.22 (s).

Homopolymerization of Ethylene

Examples 1 to 9

6.0 μmol (in 1.0 ml of 6.0 M methylene chloride solution) of each of Compounds 1 to 6 (Examples 1-4, 6 and 8) and 0.75 μmol (in 1.0 ml of 0.75 M methylene chloride solution) of each of Compounds 4 to 6 (Examples 5, 7 and 9) were placed in the 50 ml-volume stainless autoclave. After fully drying the autoclave at 120° C., it was cooled to room temperature in a dryer to distil away the methylene chloride under reduced pressure. Toluene (15 ml) was added thereto to solve the catalyst, and ethylene (3 MPa) was injected to allow the solutions to react at 80° C. (or 100° C.) for one hour or three hours. The results are shown in Table 1.

TABLE 1

|  | Catalyst (μmol) | Polymerization time (h) | Activity (kgmol$^{-1}$h$^{-1}$) | Molecular weight (Mn) (×10$^3$) | Molecular weight distribution (Mw/Mn) |
| --- | --- | --- | --- | --- | --- |
| Example 1 | Compound 1 (6.0) | 3 | 63 | 0.8 (1.8) | 1.8 |
| Example 2 | Compound 2 (6.0) | 3 | 36 | 16 (38) | 2.5 |
| Example 3 | Compound 3 (6.0) | 1 | 130 | 0.9 (1.9) | 1.8 |

TABLE 1-continued

|  | Catalyst (μmol) | Polymerization time (h) | Activity (kgmol$^{-1}$h$^{-1}$) | Molecular weight (Mn) (×10$^3$) | Molecular weight distribution (Mw/Mn) |
|---|---|---|---|---|---|
| Example 4 | Compound 4 (6.0) | 1 | 340 | 39 (91) | 2.3 |
| Example 5*[1] | Compound 4 (0.75) | 1 | 1900 | 15 (34) | 2.6 |
| Example 6*[2] | Compound 5 (6.0) | 1 | 180 | 12 (27) | 3.6 |
| Example 7*[1] | Compound 5 (0.75) | 1 | 1300 | 25 (58) | 1.9 |
| Example 8 | Compound 6 (6.0) | 1 | 350 | 39 (92) | 2.6 |
| Example 9*[1] | Compound 6 (0.75) | 1 | 2800 | 29 (69) | 2.1 |

*[1]The reaction was performed at 100° C.
*[2]The reaction was performed in a mixed solution of 1 ml of methylene chloride and 14 ml of toluene instead of using 15 ml of toluene.
*[3]The value adjusted by applying Mark-Houwink parameters. The values in parentheses are the values in terms of polystyrene before the adjustment.

Table 1 shows that among Compounds 1 to 4, Compound 4, in which both of phosphorus atoms are substituted with a branched alkyl group, gives a high-molecular-weight polymers as well as having very high catalytic activity. Also, according to the quantitative analysis based on $^{13}$C-NMR spectrum, the polymer obtained by using Compound 4 had only about one methyl branch per 1,000 carbon atoms, and a highly linear polyethylene was obtained.

Compounds 5 and 6, in which a catalyst precursor had been changed, also showed a very high catalytic activity.

The $^{13}$C-NMR spectrum chart of the product in Example 5 is shown in FIG. 1.

Copolymerization of Ethylene and Vinyl Acetate

Example 10

Compound 4, toluene, ethylene (3 MPa) and vinyl acetate in amounts as in Table 2 were put in a stainless steel autoclave to perform a polymerization reaction at a temperature for a period of time as described in the table.

Figure 2:
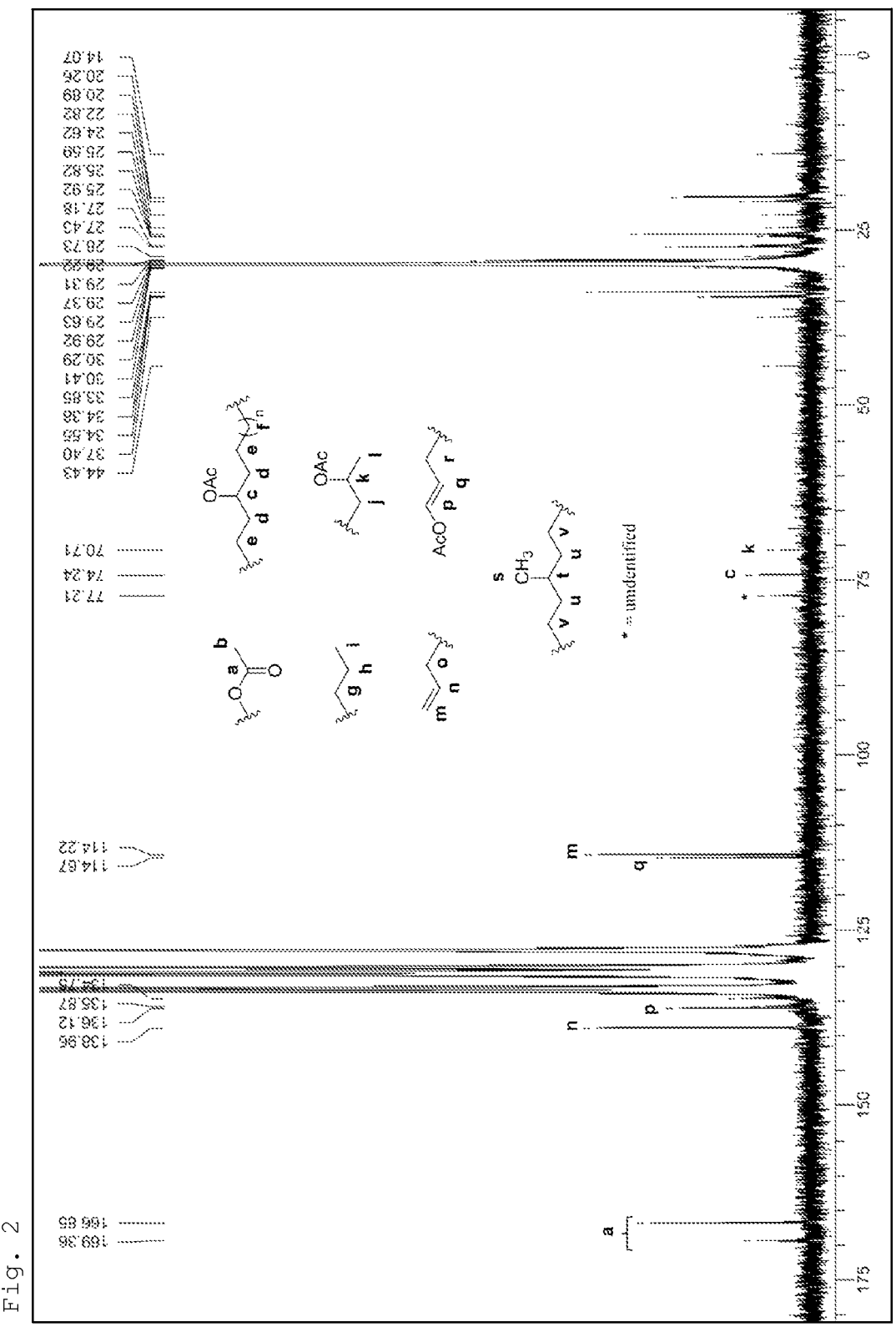

The $^{13}$C-NMR spectrum chart of the product in Example 10 is shown in FIG. 2.

Example 11

The catalyst was changed to Compound 6 and the polymerization reaction was performed in a similar manner to that in Example 10 under conditions as described in Table 2.

Although there have been few reports on coordination-insertion polymerization using a comonomer with vinyl acetate, the progress of copolymerization was confirmed in both cases of using Compound 4 and using Compound 6. The result of the quantitative analysis based on $^{13}$C-NMR spectrum of the obtained polymer confirmed that a vinyl acetate monomer was incorporated in both terminals of the polymer chain as well as in the main chain.

Copolymerization of Ethylene and Allyl Acetate

Example 12

Compound 4, toluene, ethylene (3 MPa) and allyl acetate in amounts as in Table 2 were put in a stainless steel autoclave to perform a polymerization reaction at a temperature for a period of time as described in the table.

Figure 3:
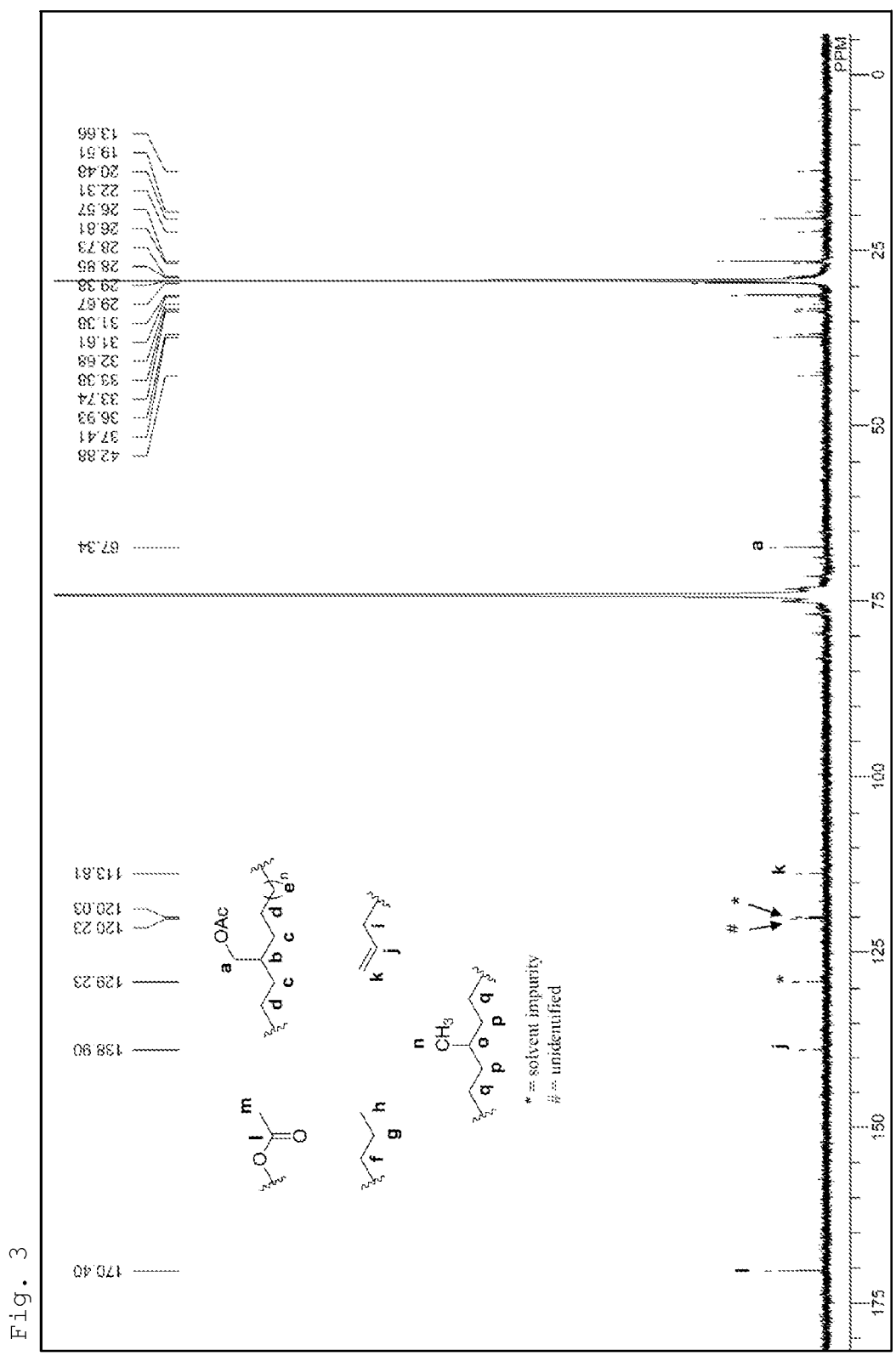

The $^{13}$C-NMR spectrum chart of the product in Example 12 is shown in FIG. 3.

Example 13

The catalyst was changed to Compound 6 and the polymerization reaction was performed in a similar manner to that in Example 12 under conditions as described in Table 2.

The progress of copolymerization of ethylene and allyl acetate was confirmed in both cases of using Compound 4 and using Compound 6. The molecular weight (Mn) of the polymer obtained by using Compound 6 was about twice as much as that reported in the case of a catalyst of phosphine-sulfonic acid ester ligand (J. Am. Chem. Soc. 2011, 133, 1232).

Copolymerization of Ethylene and Allyl Chloride

Example 14

Figure 4:
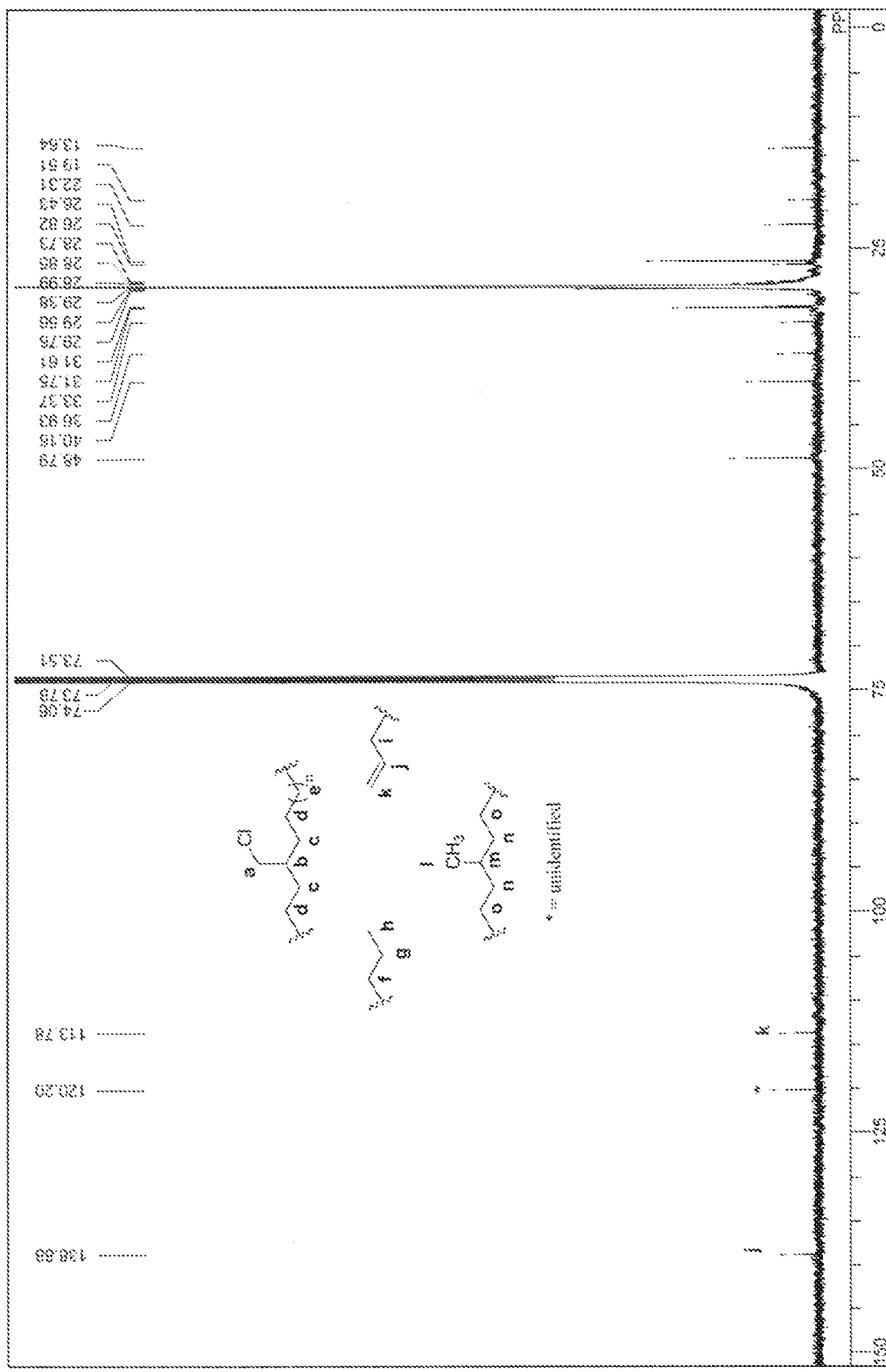

Compound 4, toluene, ethylene (3 MPa) and allyl chloride in amounts as in Table 2 were put in a stainless steel autoclave to perform a polymerization reaction at a temperature for a period of time as described in the table. The $^{13}$C-NMR spectrum chart of the product in Example 14 is shown in FIG. 4.

Example 15

The catalyst was changed to Compound 6 and the polymerization reaction was performed in a similar manner to that in Example 14 under conditions as described in Table 2.

The progress of copolymerization of ethylene and allyl chloride was confirmed in both cases of using Compound 4 and using Compound 6. The amount of the incorporated polar monomer was nearly equal to that in the above-mentioned report on the catalyst of phosphine-sulfonic acid ester ligands, and the molecular weight (Mn) of the polymer was about twice as much as that in the report.

Copolymerization of Ethylene and Acrylonitrile

Example 16

Figure 5:
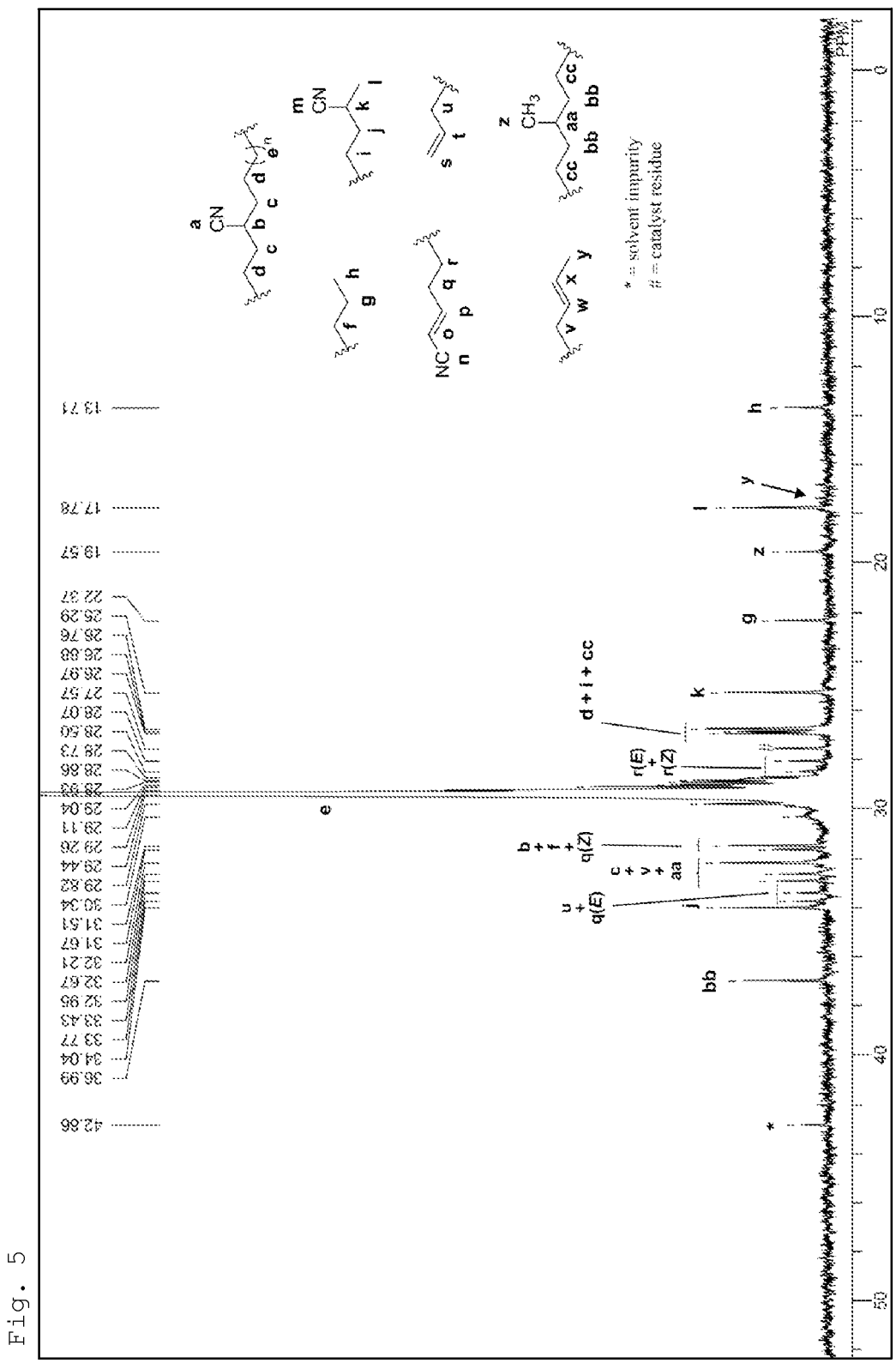

Compound 4, toluene, ethylene (3 MPa) and acrylonitrile in amounts as in Table 2 were put in a stainless steel autoclave to perform a polymerization reaction at a temperature for a period of time as described in the table. The $^{13}$C-NMR spectrum chart of the product in Example 16 is shown in FIG. 5.

Example 17

The catalyst was changed to Compound 6 and the polymerization reaction was performed in a similar manner to that in Example 16 under conditions as described in Table 2.

The progress of copolymerization of ethylene and acrylonitrile was confirmed in both cases of using Compound 4 and using Compound 6. The result of the quantitative analysis based on $^{13}$C-NMR spectrum of the obtained polymers confirmed that acrylonitrile monomers were incorporated in both terminals of the polymer chain as well as in the main chain, and the amount of the incorporated monomer was 2.0 to 2.5%.

Copolymerization of Ethylene and Butyl Vinyl Ether

Example 18

Figure 6:
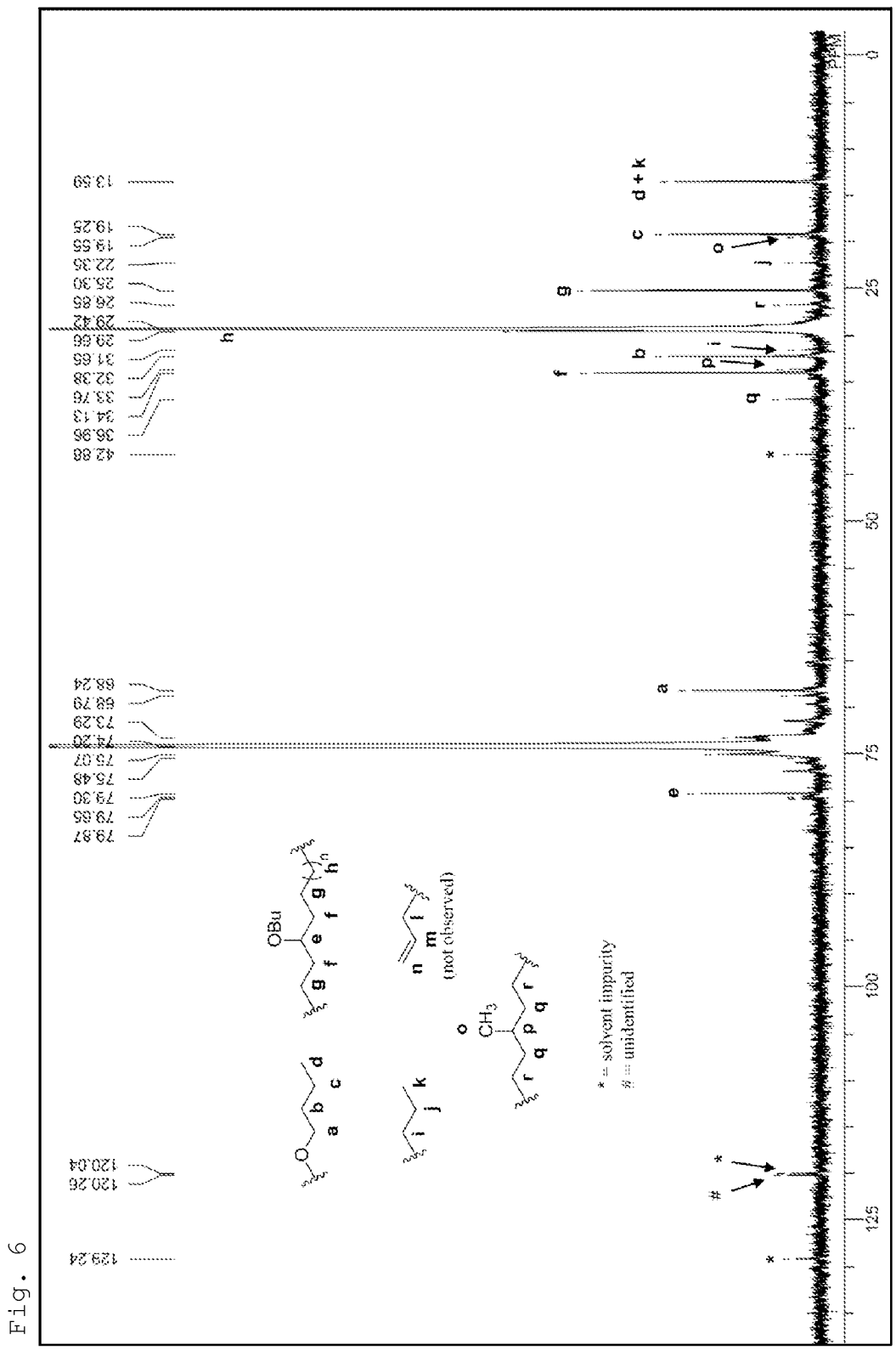

Compound 4, toluene, ethylene (3 MPa) and butyl vinyl ether in amounts as in Table 2 were put in a stainless steel autoclave to perform a polymerization reaction at a temperature for a period of time as described in the table. The $^{13}$C-NMR spectrum chart of the product in Example 18 is shown in FIG. 6.

Example 19

The catalyst was changed to Compound 6 and the polymerization reaction was performed in a similar manner to that in Example 16 under conditions as described in Table 2.

Although it has been considered the copolymerization of ethylene and vinyl ether is difficult with a conventional cationic α-diimine palladium catalyst, the progress of copolymerization of ethylene and butyl vinyl ether was confirmed in both cases of using Compound 4 and using Compound 6.

Examples 20 to 24

The catalysts in Examples 1 to 9 were changed to Compounds 7, 10, 12 and 14, and homopolyzation of ethylene was conducted in a similar manner. The polymerization conditions and the results are shown in Table 3 and Table 4, respectively.

TABLE 3

| Examples | Catalyst (μmol) | Solvent (ml) | Ethylene pressure (MPa) | Polymerization temperature (° C.) | Time (h) |
|---|---|---|---|---|---|
| 20 | Compound 7 (6.0) | Toluene (15) | 3.0 | 80 | 1 |
| 21 | Compound 7 (0.75) | Toluene (15) | 3.0 | 100 | 1 |
| 22 | Compound 10 (0.75) | Toluene (15) | 3.0 | 100 | 1 |
| 23 | Compound 12 (0.75) | Toluene (15) | 3.0 | 100 | 1 |
| 24 | Compound 14 (6.0) | Toluene (15) | 3.0 | 80 | 1 |

TABLE 2

| Examples | Catalyst (mmol) | Comonomer | Comonomer amount (ml) | Solvent amount (ml) | Temperature (° C.) | Reaction time (h) | Yield (g) | Activity (kgmol$^{-1}$h$^{-1}$) | Mn (×10$^3$) | Mw (×10$^3$) | Incorporated amount (%) | Me branch*4 (/10$^3$C) |
|---|---|---|---|---|---|---|---|---|---|---|---|---|
| 10 | Compound 4 (0.02) | Vinyl acetate | 12 | 3 | 80 | 15 | 0.21 | 0.72 | 3.4 | 2.5 | 1.3 | 1.5 |
| 11 | Compound 6 (0.01) | Vinyl acetate | 12 | 3 | 80 | 16 | 0.18 | 1.1 | 3.0 | 2.5 | 1.4 | 1.7 |
| 12 | Compound 4 (0.01) | Allyl acetate | 3 | 12 | 80 | 12 | 0.18 | 1.4 | 17 | 2.7 | 1.0 | 1.0 |
| 13 | Compound 6 (0.01) | Allyl acetate | 3 | 12 | 80 | 12 | 0.94 | 7.6 | 35 | 2.2 | 1.2 | 0.7 |
| 14 | Compound 4 (0.02) | Allyl chloride | 3 | 12 | 80 | 20 | 0.12 | 0.31 | 13 | 1.9 | 1.1 | 1.0 |
| 15 | Compound 6 (0.01) | Allyl chloride | 3 | 12 | 80 | 20 | 0.18 | 0.93 | 20 | 2.9 | 0.7 | 0.6 |
| 16 | Compound 4 (0.01) | Acrylonitrile | 2.5 | 2.5 | 100 | 86 | 0.50 | 0.58 | 3.5 | 2.4 | 2.1 | 1.8 |
| 17 | Compound 6 (0.006) | Acrylonitrile | 2.5 | 2.5 | 100 | 72 | 0.30 | 0.69 | 3.5 | 2.7 | 2.5 | 0.1 |
| 18 | Compound 4 (0.02) | Butyl vinyl ether | 5 | 10 | 80 | 21 | 0.28 | 0.66 | 21 | 1.9 | 2.0 | 1.4 |
| 19 | Compound 6 (0.01) | Butyl vinyl ether | 5 | 10 | 80 | 20 | 0.23 | 1.2 | 19 | 2.4 | 4.1 | 0.5 |

*4The number of methyl branches per 1,000 carbon atoms in the polymer was determined by the quantitative analysis of $^{13}$C NMR spectrum.

TABLE 4

| Examples | Yield (g) | Activity (kgmol$^{-1}$h$^{-1}$) | Weight-average molecular weight (Mw) | Number-average molecular weight (Mn) | Mw/Mn |
|---|---|---|---|---|---|
| 20 | 1.8 | 300 | 331,000 | 138,000 | 2.4 |
| 21 | 2.0 | 2,700 | 166,000 | 77,000 | 2.2 |

TABLE 4-continued

| Examples | Yield (g) | Activity (kgmol$^{-1}$h$^{-1}$) | Weight-average molecular weight (Mw) | Number-average molecular weight (Mn) | Mw/Mn |
|---|---|---|---|---|---|
| 22 | 1.7 | 2,200 | 86,000 | 21,000 | 4.1 |
| 23 | 0.37 | 490 | 160,000 | 80,000 | 2.0 |
| 24 | 1.0 | 168 | 160,000 | 57,000 | 2.8 |

Examples 25 to 28

The catalysts in Examples 12 and 13 were changed to Compounds 7, 10 and 14, and the copolymerization of ethylene and allyl acetate was conducted in a similar manner, or under conditions in which the ethylene pressure, scale or reaction time was changed. The polymerization conditions and results are shown in Table 5 and Table 6, respectively.

TABLE 5

| Examples | Catalyst (µmol) | Allyl acetate (ml) | Toluene (ml) | Ethylene pressure (MPa) | Polymerization temperature (° C.) | Time (h) |
|---|---|---|---|---|---|---|
| 25 | Compound 7 (10) | 3 | 12 | 3.0 | 80 | 12 |
| 26 | Compound 7 (10) | 18.8 | 56.3 | 4.0 | 80 | 5 |
| 27 | Compound 10 (10) | 3 | 12 | 3.0 | 80 | 12 |
| 28 | Compound 14 (10) | 3 | 12 | 3.0 | 80 | 14 |

TABLE 6

| Examples | Yield (g) | Activity (kgmol$^{-1}$h$^{-1}$) | Weight-average molecular weight (Mw) | Number-average molecular weight (Mn) | Mw/Mn | AAC content (mol %) |
|---|---|---|---|---|---|---|
| 25 | 0.78 | 6.5 | 67,000 | 29,000 | 2.3 | 1.2 |
| 26 | 0.52 | 10 | 61,000 | 29,000 | 2.1 | 1.2 |
| 27 | 0.35 | 2.9 | 24,000 | 12,000 | 2.0 | 1.3 |
| 28 | 0.23 | 1.6 | 62,000 | 22,000 | 2.8 | 3.8 |

Example 29

In the copolymerization of ethylene and allyl acetate using Compound 6 as a catalyst, a scaled up and longtime reaction was performed. That is, Compound 6 (0.029 g, 0.020 mmol), toluene (225 ml) and allyl acetate (75 ml) were added into a 500 ml-volume autoclave, ethylene was filled until the pressure reached 4.0 MPa, and the solution was stirred at 80° C. for 91 hours. After being cooled to room temperature, the reaction solution was added to methanol (1.5 l). The precipitated polymer was collected by filtration and dried under reduced pressure. The yield was 14.9 g and the catalytic activity was calculated to be 8.2 kgmol$^{-1}$ h$^{-1}$. As to the molecular weight of the obtained polymer in terms of polystyrene, the weight average molecular weight (Mw), number average molecular weight (Mn) and Mw/Mn were calculated to be 67,000, 32,000 and 2.1, respectively.

Example 30

Homopolyzation of ethylene was conducted using a reaction solution, in which Compound 8 and sodium tetrakis[3,5-bis(trifluoromethyl)phenyl]borate were reacted in advance, as a catalyst solution. A toluene solution (30 ml) of Compound 8 (5.1 mg, 0.010 mmol) and sodium tetrakis[3,5-bis(trifluoromethyl)phenyl]borate (9.7 mg, 0.011 mmol) was stirred under argon atmosphere at room temperature for 30 minutes and the solution was used as a catalyst solution. At that time, it is assumed that an organometallic compound of formula (II) in which $R^4$ does not exist, i.e.: an organometallic compound represented by the following formula is generated.

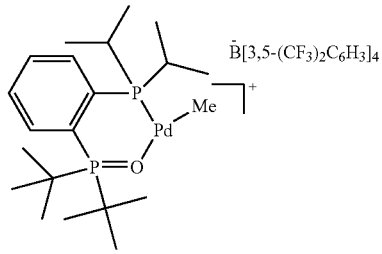

Note that, here, a compound corresponding to Compound 8 ($R^{1a}=R^{1b}$=an isopropyl group, $R^{2a}=R^{2b}$=a t-butyl group, $A^1$=an orthophenylene group) is described.

Next, the total amount of the catalyst solution and toluene (45 ml) were added into a 120 ml-volume autoclave, and after filling ethylene until the pressure reached 3.0 MPa, the solution was stirred at 80° C. for one hour. After being cooled to room temperature, the reaction solution was added to methanol (300 ml). The precipitated polymer was collected by filtration and dried under reduced pressure. The yield was 5.4 g and the catalytic activity was calculated to be 540 kgmol$^{-1}$ h$^{-1}$. As to the molecular weight of the obtained polymer in terms of polystyrene, the weight average molecular weight (Mw), number average molecular weight (Mn) and Mw/Mn were calculated to be 485,000, 211,000 and 2.3, respectively. The amount of the incorporated allyl acetate was calculated to be 1.4 mol % based on the $^1$H-NMR spectrum using 1,1,2,2-tetrachloroethane-d2 as a solvent.

Example 31

Copolymerization of ethylene and allyl acetate was performed using a catalyst solution prepared in a similar manner to that described in Example 30. That is, a total amount of the catalyst solution obtained by stirring a toluene solution (30 ml) of Compound 8 (5.1 mg, 0.010 mmol) and sodium tetrakis[3,5-bis(trifluoromethyl)phenyl]borate (9.7 mg, 0.011 mmol) at room temperature for 30 minutes; toluene (26.3 ml) and allyl acetate (18.8 ml) were added into a 120 ml-volume autoclave; and after ethylene was filled until the pressure reached 4.0 MPa, the solution was stirred at 80° C. for five hours. After being cooled to room temperature, the reaction solution was added to methanol (300 ml). The precipitated polymer was collected by filtration and dried under reduced pressure. The yield was 0.23 g and the catalytic activity was calculated to be 4.7 kgmol$^{-1}$ h$^{-1}$. As to the molecular weight of the obtained polymer in terms of polystyrene, the weight average molecular weight (Mw), number average molecular weight (Mn) and Mw/Mn were calculated to be 58,000, 28,000 and 2.1, respectively. The amount of the incorporated allyl acetate was calculated to be 1.1 mol % based on the $^1$H-NMR spectrum using 1,1,2,2-tetrachloroethane-d2 as a solvent.

Examples 32 to 37

Homopolymerization of ethylene, copolymerization of ethylene and allyl acetate, copolymerization of ethylene and butyl vinyl ether, and copolymerization of ethylene and methyl acrylate were conducted using Compound 10; Compound 16; and Compound 17 which was synthesized by a similar synthesis method to that of Compound 16. The polymerization conditions and results are shown in Table 7 and Table 8, respectively.

TABLE 7

| Examples | Catalyst (μmol) | Polar olefin kind (ml) | Toluene (ml) | Ethylene pressure (MPa) | Polymerization temperature (° C.) | Time (h) |
|---|---|---|---|---|---|---|
| 32 | Compound 16 (0.75) | None | 15 | 3.0 | 100 | 1 |
| 33 | Compound 17 (0.75) | None | 15 | 3.0 | 80 | 1 |
| 34 | Compound 16 (10) | Allyl acetate (3) | 12 | 3.0 | 80 | 12 |
| 35 | Compound 10 (10) | Butyl vinyl ether (5) | 10 | 3.0 | 80 | 26 |
| 36 | Compound 16 (10) | Butyl vinyl ether (5) | 10 | 3.0 | 80 | 20 |
| 37 | Compound 16 (10) | Methyl acrylate (2.5) | 2.5 | 3.0 | 80 | 15 |

TABLE 8

| Examples | Yield (g) | Activity (kgmol$^{-1}$h$^{-1}$) | Weight-average molecular weight (Mw) | Number-average molecular weight (Mn) | Mw/Mn | Polar monomer content (mol %) |
|---|---|---|---|---|---|---|
| 32 | 1.6 | 2,200 | 110,000 | 37,000 | 2.9 | — |
| 33 | 0.53 | 710 | 270,000 | 130,000 | 2.1 | — |
| 34 | 0.18 | 1.5 | 20,000 | 8,900 | 2.3 | 0.40 |
| 35 | 0.20 | 0.76 | 29,000 | 13,000 | 2.2 | 1.0 |
| 36 | 0.070 | 0.35 | 22,000 | 9,300 | 2.4 | 0.6 |
| 37 | 0.040 | 0.24 | 15,000 | 6,900 | 2.2 | 8.6 |

As discussed above, it was confirmed that the novel metal compound of the present invention is very useful as a catalyst for copolymerization of ethylene and various polar monomers. By using a catalyst composition containing the novel metal compound of the present invention, a highly-linear polymer can be obtained and it is possible to obtain a copolymer in which a polar monomer is randomly distributed in a polymer chain. Thus, the catalyst composition of the present invention is industrially very useful because it enables the production of an industrially-useful functionalized polyolefin.

The invention claimed is:

1. A method for producing copolymers, comprising a process of reacting non-polar olefins with polar olefins under polymerization conditions in the presence of a catalyst composition containing an organometallic compound, wherein polar olefins are represented by formula (VII)

$$CH_2=CR^{13}R^{14} \qquad (VII)$$

wherein $R^{13}$ represents a hydrogen atom or a methyl group; $R^{14}$ represents —COOR$^{15}$, —CN, —OCOR$^{15}$, —OR$^{15}$, —CH$_2$—OCOR$^{15}$, —CH$_2$OH, —CH$_2$—N(R$^{16}$)$_2$ or —CH$_2$—Hal, wherein $R^{15}$ represents a hydrogen atom, an alkyl group having 1 to 5 carbon atoms or an aryl group having 6 to 18 carbon atoms; $R^{16}$ represents a hydrogen atom, an alkyl group having 1 to 5 carbon atoms, an aryl group having 6 to 18 carbon atoms or an alkoxycarbonyl group; and Hal represents a halogen atom, and wherein the organometallic compound contains bisphosphine monoxide (BPMO) represented by formula (I) and a metal center M comprising elements belonging to Group 10 in the periodic system that forms a complex with BPMO

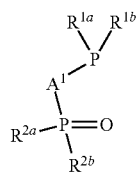

(I)

$R^{1a}$, $R^{1b}$, $R^{2a}$ and $R^{2b}$ may be the same or different with each other, and independently represent a substituted or unsubstituted alkyl group having 1 to 14 carbon atoms, a substituted or unsubstituted cycloalkyl group having 3 to 14 carbon atoms, a substituted or unsubstituted biphenyl group or a substituted or unsubstituted aryl group; a pair of $R^{1a}$ and $R^{1b}$ and a pair of $R^{2a}$ and $R^{2b}$ may be bonded to form a ring structure; and $A^1$ represents an arylene group, a monocyclic heteroarylene group, a bivalent heterocyclic group, an alkylene group having 1 to 2 carbon atoms, a cycloalkylene group having 3 to 10 carbon atoms, an alkenylene group having 2 to 8 carbon atoms, or a cycloalkenylene group having 3 to 10 carbon atoms.

2. The method for producing copolymers as claimed in claim 1, wherein both of $R^{1a}$ and $R^{1b}$ are isopropyl group or t-butyl group.

3. The method for producing copolymers as claimed in claim 1, wherein both of $R^{2a}$ and $R^{2b}$ are t-butyl group.

4. The method for producing copolymers as claimed in claim claim 1, wherein $R^{14}$ is CH$_2$—OCOR$^{15}$, CH$_2$OH, —CH$_2$—N(R$^{16}$)$_2$ or —CH$_2$—Hal.

5. The method for producing copolymers as claimed in claim 1, wherein the organometallic compound is represented by formula (II)

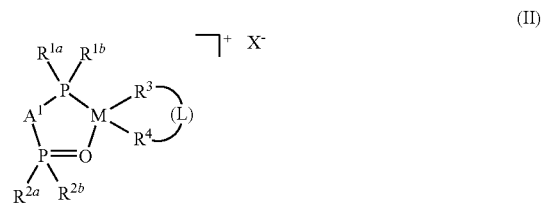

(II)

wherein

M represents an element belonging to Group 10 in the periodic system;

$R^{1a}$, $R^{1b}$, $R^{2a}$ and $R^{2b}$ may be the same or different with each other, and independently represent a substituted or unsubstituted alkyl group having 1 to 14 carbon atoms, a substituted or unsubstituted cycloalkyl group having 3 to 14 carbon atoms, a substituted or unsubstituted biphenyl group or a substituted or unsubstituted aryl group; a pair of $R^{1a}$ and $R^{1b}$ and a pair of $R^{2a}$ and $R^{2b}$ may be bonded to form a ring structure;

$A^1$ represents an arylene group, a monocyclic heteroarylene group, a bivalent heterocyclic group, an alkylene group having 1 to 2 carbon atoms, a cycloalkylene group having 3 to 10 carbon atoms, an alkenylene group having 2 to 8 carbon atoms, or a cycloalkenylene group having 3 to 10 carbon atoms;

$R^3$ represents a hydrogen atom, an alkyl group having 1 to 10 carbon atoms, an alkenyl group having 2 to 10 carbon atoms or a bivalent group represented by $A^2$ ($A^2$ represents an arylene group, a monocyclic heteroarylene group, a monocyclic cycloalkylene group, a monocyclic cycloalkenylene group, a monocyclic heterocycloalkylene group, a monocyclic heterocycloalkenylene group, a heterocyclic group or a C2-C4 alkylene group;

$R^4$ represents a neutral electron-donating ligand; $R^3$ and $R^4$ may be crosslinked; when $R^3$ and $R^4$ are crosslinked, L represents a single bond or a bivalent group selected from an alkylene group, a haloalkylene group, an alkenylene group or an alkynylene group; and when $R^3$ and $R^4$ are not crosslinked (that is, when L does not exist), $R^4$ needs not to exist; and X$^-$ represents a counterion of the cationic organometallic compound.

6. The method for producing copolymers as claimed in claim 5, wherein ligand $R^4$ is:

(i) selected from pyridine, a substituted pyridine, a nitrile compound, ammonia, an alkylamine, a substituted alkylamine, an arylamine or a substituted arylamine; or (ii) represented by formula (1)

(1)

(wherein W represents C or S; Z is selected from O, S, NH or NR$^a$ (R$^a$ represents an alkyl group or an aryl group) and Y needs not to exist; when Y exists, Y is selected from O, S, NH or NR$^b$ (R$^b$ represents an alkyl group or an aryl group); R$^5$ represents a substituted or unsubstituted alkyl group having 1 to 10 carbon atoms, —OR$^c$ (R$^c$ represents an alkyl group or an aryl group) or —NR$^d_2$ (R$^d$ represents an alkyl group or an aryl group).

7. The method for producing copolymers as claimed in claim 1, wherein the organometallic compound is represented by formula (IIa)

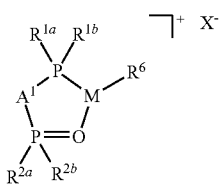

(IIa)

wherein
M represents an element belonging to Group 10 in the periodic system;
R$^{1a}$, R$^{1b}$, R$^{2a}$ and R$^{2b}$ may be the same or different with each other, and independently represent a substituted or unsubstituted alkyl group having 1 to 14 carbon atoms, a substituted or unsubstituted cycloalkyl group having 3 to 14 carbon atoms, a substituted or unsubstituted biphenyl group or a substituted or unsubstituted aryl group; a pair of R$^{1a}$ and R$^{1b}$ and a pair of R$^{2a}$ and R$^{2b}$ may be bonded to form a ring structure;
R$^6$ represents an alkyl group having 1 to 10 carbon atoms, an alkenyl group or an aryl group;
A$^1$ represents an arylene group, a monocyclic heteroarylene group, a bivalent heterocyclic group, an alkylene group having 1 to 2 carbon atoms, a cycloalkylene group having 3 to 10 carbon atoms, an alkenylene group having 2 to 8 carbon atoms, or a cycloalkenylene group having 3 to 10 carbon atoms; and
X$^-$ represents a counterion of the cationic organometallic compound.

8. The method for producing copolymers as claimed in claim 7, wherein A$^1$ is a substituted or unsubstituted phenylene group, a substituted or unsubstituted naphthylene group or substituted or an unsubstituted methylene group.

9. The method for producing copolymers as claimed in claim 7, wherein R$^{1a}$, R$^{1b}$, R$^{2a}$ and R$^{2b}$ independently represent a branched alkyl group having 3 to 6 carbon atoms.

10. The method for producing copolymers as claimed in claim 7, wherein X— is selected from SbF$_6^-$, BPh$_4^-$, BArF$_4^-$ (ArF$_4$ is [3,5-(CF$_3$)$_2$C$_6$H$_3$]$_4$), BF$_4^-$ or PF$_6^-$.

11. The method for producing copolymers as claimed in claim 7, wherein M is palladium.

12. The method for producing copolymers as claimed in claim 1, wherein the organometallic compound is represented by formula (III)

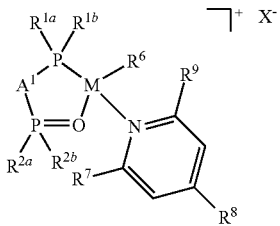

(III)

wherein
M represents an element belonging to Group 10 in the periodic system;
R$^{1a}$, R$^{1b}$, R$^{2a}$ and R$^{2b}$ may be the same or different with each other, and independently represent a substituted or unsubstituted alkyl group having 1 to 14 carbon atoms, a substituted or unsubstituted cycloalkyl group having 3 to 14 carbon atoms, a substituted or unsubstituted biphenyl group or a substituted or unsubstituted aryl group; a pair of R$^{1a}$ and R$^{1b}$ and a pair of R$^{2a}$ and R$^{2b}$ may be bonded to form a ring structure;
A$^1$ represents an arylene group, a monocyclic heteroarylene group, a bivalent heterocyclic group, an alkylene group having 1 to 2 carbon atoms, a cycloalkylene group having 3 to 10 carbon atoms, an alkenylene group having 2 to 8 carbon atoms, or a cycloalkenylene group having 3 to 10 carbon atoms;
X$^-$ represents a counterion of the cationic organometallic compound;
R$^6$ represents an alkyl group having 1 to 10 carbon atoms, an alkenyl group or an aryl group; R$^7$, R$^8$ and R$^9$ independently represent an alkyl group or an alkoxy group having 1 to 4 carbon atoms.

13. The method for producing copolymers as claimed in claim 12, wherein A$^1$ is a substituted or unsubstituted phenylene group, a substituted or unsubstituted naphthylene group or a substituted or unsubstituted methylene group.

14. The method for producing copolymers as claimed in claim 12, wherein R$^{1a}$, R$^{1b}$, R$^{2a}$ and R$^{2b}$ independently represent a branched alkyl group having 3 to 6 carbon atoms.

15. The method for producing copolymers as claimed in claim 12, wherein X$^-$ is selected from SbF$_6^-$, BPh$_4^-$, BArF$_4^-$ (ArF$_4$ is [3,5-(CF$_3$)$_2$C$_6$H$_3$]$_4$), BF$_4^-$ and or PF$_6^-$.

16. The method for producing copolymers as claimed in claim 12, wherein M is palladium.

17. The method for producing copolymers as claimed in claim 1, wherein the organometallic compound is represented by formula (IV)

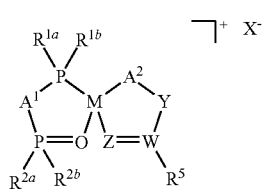

(IV)

wherein
M represents an element belonging to Group 10 in the periodic system;
R$^{1a}$, R$^{1b}$, R$^{2a}$ and R$^{2b}$ may be the same or different with each other, and independently represent a substituted or unsubstituted alkyl group having 1 to 14 carbon atoms, a substituted or unsubstituted cycloalkyl group having 3 to 14 carbon atoms, a substituted or unsubstituted biphenyl group or a substituted or unsubstituted aryl group; a pair of R$^{1a}$ and R$^{1b}$ and a pair of R$^{2a}$ and R$^{2b}$ may be bonded to form a ring structure;
A$^1$ represents an arylene group, a monocyclic heteroarylene group, a bivalent heterocyclic group, an alkylene group having 1 to 2 carbon atoms, a cycloalkylene group having 3 to 10 carbon atoms, an alkenylene group having 2 to 8 carbon atoms, or a cycloalkenylene group having 3 to 10 carbon atoms;
A$^2$ represents an arylene group, a monocyclic heteroarylene group, a monocyclic cycloalkylene group, a monocyclic cycloalkenylene group, a monocyclic heterocycloalkylene group, a monocyclic heterocycloalkenylene group, a heterocyclic group or a C2-C4 alkylene group;

X⁻ represents a counterion of the cationic organometallic compound;

W represents C or S;

Z is selected from O, S, NH or NR$^a$ (R$^a$ represents an alkyl group or an aryl group) and Y needs not to exist; when Y exists, Y is selected from O, S, NH or NR$^b$ (R$^b$ represents an alkyl group or an aryl group); and R$^5$ represents a substituted or unsubstituted alkyl group having 1 to 10 carbon atoms, —OR$^c$ (R$^c$ represents an alkyl group or an aryl group) or —NR$^d_2$ (R$^d$ represents an alkyl group or an aryl group).

18. The method for producing copolymers as claimed in claim 17, wherein the organometallic compound is represented by formula (V)

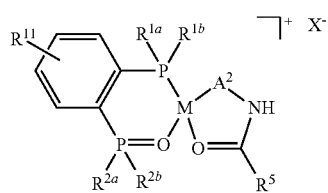

(V)

wherein
M represents an element belonging to Group 10 in the periodic system;

R$^{1a}$, R$^{1b}$, R$^{2a}$ and R$^{2b}$ may be the same or different with each other, and independently represent a substituted or unsubstituted alkyl group having 1 to 14 carbon atoms, a substituted or unsubstituted cycloalkyl group having 3 to 14 carbon atoms, a substituted or unsubstituted biphenyl group or a substituted or unsubstituted aryl group; a pair of R$^{1a}$ and R$^{1b}$ and a pair of R$^{2a}$ and R$^{2b}$ may be bonded to form a ring structure;

A$^2$ represents an arylene group, a monocyclic heteroarylene group, a monocyclic cycloalkylene group, a monocyclic cycloalkenylene group, a monocyclic heterocycloalkylene group, a monocyclic heterocycloalkenylene group, a heterocyclic group or a C2-C4 alkylene group;

R$^5$ represents a substituted or unsubstituted alkyl group having 1 to 10 carbon atoms, —OR$^c$, wherein R$^c$ represents an alkyl group or an aryl group) or —NR$^d_2$ and wherein R$^d$ represents an alkyl group or an aryl group;

X⁻ represents a counterion of the cationic organometallic compound; and

R$^{11}$ may not exist or represents an alkyl group having 1 to 10 carbon atoms, 1 to 4 of which exist on a benzene ring, and the existing two or more R$^{11}$'s may be the same or different with each other.

19. The method for producing copolymers as claimed in claim 18, wherein the organometallic compound is represented by formula (VI)

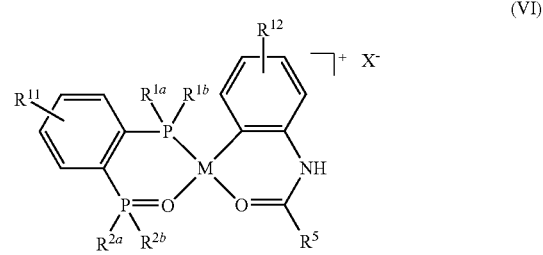

(VI)

wherein
M represents an element belonging to Group 10 in the periodic system;

R$^{1a}$, R$^{1b}$, R$^{2a}$ and R$^{2b}$ may be the same or different with each other, and independently represent a substituted or unsubstituted alkyl group having 1 to 14 carbon atoms, a substituted or unsubstituted cycloalkyl group having 3 to 14 carbon atoms, a substituted or unsubstituted biphenyl group or a substituted or unsubstituted aryl group; a pair of R$^{1a}$ and R$^{1b}$ and a pair of R$^{2a}$ and R$^{2b}$ may be bonded to form a ring structure;

R$^5$ represents a substituted or unsubstituted alkyl group having 1 to 10 carbon atoms, —OR$^c$, wherein R$^c$ represents an alkyl group or an aryl group) or —NR$^d_2$ and wherein R$^d$ represents an alkyl group or an aryl group;

R$^{11}$ may not exist or represents an alkyl group having 1 to 10 carbon atoms, 1 to 4 of which exist on a benzene ring, and the existing two or more R$^{11}$'s may be the same or different with each other; R$^{12}$ does not exist, or represents an alkyl group having 1 to 10 carbon atoms, which is substituted with an arbitrary replaceable hydrogen in a benzene ring, and when two or more R$^{12}$ exist, they be the same or different from each other; and X⁻ represents a counterion of the cationic organometallic compound.

20. The method for producing copolymers as claimed in claim 17, wherein R$^{1a}$, R$^{1b}$, R$^{2a}$ and R$^{2b}$ are independently a branched alkyl group having 3 to 14 carbon atoms.

21. The compound method for producing copolymers as claimed in claim 17, wherein X⁻ is selected from SbF$_6^-$, BPh$_4^-$, BArF$_4^-$ where ArF$_4$ is [3,5-(CF$_3$)$_2$C$_6$H$_3$]$_4$, BF$_4^-$ or PF$_6^-$.

* * * * *